US011577080B2

(12) United States Patent
Conde et al.

(10) Patent No.: US 11,577,080 B2
(45) Date of Patent: Feb. 14, 2023

(54) NEUROMODULATION DEVICE AND METHOD FOR TREATING METABOLIC DISORDERS

(71) Applicants: GALVANI BIOELECTRONICS LIMITED, Brentford, Middlesex (GB); FACULDADE DE CIÊNCIAS MÉDICAS DA UNIVERSIDADA NOVA DE LISBOA, Lisbon (PT)

(72) Inventors: Silvia Margarida Vilares Santos Conde, Lisbon (PT); Daniel John Chew, Stevenage (GB); Hans Jakob Kristoffer Famm, Stevenage (GB); Maria Pedro Sucena Guarino, Lisbon (PT); Brad Holinski, San Jose, CA (US); Sonal Patel, Stevenage (GB)

(73) Assignees: Presidio Medical, Inc., South San Francisco, CA (US); Faculdade De Ciências Médicas Da Universidade Nova De Lisboa, Lisbon (PT)

( * ) Notice: Subject to any disclaimer, the term of this patent is extended or adjusted under 35 U.S.C. 154(b) by 0 days.

(21) Appl. No.: 15/523,914

(22) PCT Filed: Nov. 3, 2015

(86) PCT No.: PCT/PT2015/000047
§ 371 (c)(1),
(2) Date: May 2, 2017

(87) PCT Pub. No.: WO2016/072875
PCT Pub. Date: May 12, 2016

(65) Prior Publication Data
US 2017/0333708 A1 Nov. 23, 2017

Related U.S. Application Data
(60) Provisional application No. 62/074,136, filed on Nov. 3, 2014.

(51) Int. Cl.
A61N 1/36 (2006.01)
A61N 1/05 (2006.01)

(52) U.S. Cl.
CPC ........... *A61N 1/36085* (2013.01); *A61N 1/36* (2013.01); *A61N 1/3605* (2013.01);
(Continued)

(58) Field of Classification Search
None
See application file for complete search history.

(56) References Cited

U.S. PATENT DOCUMENTS 5,231,988 A * 8/1993 Wernicke ........... A61N 1/36053
600/319
5,299,569 A * 4/1994 Wernicke ........... A61N 1/36082
600/544
(Continued)

FOREIGN PATENT DOCUMENTS

WO 2008024557 A1 2/2008
WO 2011156439 A3 12/2011
(Continued)

OTHER PUBLICATIONS

Camilleri et. al, "Selection of electrical algorithms to treat obesity with intermittent vagal block using an implantable medical device". Surgery for Obesity and Related Diseases, vol. 5, No. 2, 2009, pp. 224-229.
(Continued)

*Primary Examiner* — Kennedy Schaetzle
(74) *Attorney, Agent, or Firm* — Knobbe Martens Olson & Bear, LLP

(57) ABSTRACT

The invention refers to a device for inhibiting the neural activity of a carotid sinus nerve (CSN) or carotid body of a subject, the device comprising: one or more transducers configured to apply a signal to the CSN or associated carotid
(Continued)

body of the subject, optionally at least two such transducers; and a controller coupled to the one or more transducers, the controller controlling the signal to be applied by the one or more transducers, such that the signal inhibits the neural activity of the CSN or carotid body to produce a physiological response in the subject, wherein the physiological response is one or more of the group consisting of: an increase in insulin sensitivity in the subject, an increase in glucose tolerance in the subject, a decrease in (fasting) plasma glucose concentration in the subject, a reduction in subcutaneous fat content in the subject, and a reduction in obesity in the subject.

23 Claims, 18 Drawing Sheets

(52) U.S. Cl.
CPC ....... *A61N 1/3606* (2013.01); *A61N 1/36034* (2017.08); *A61N 1/36171* (2013.01); *A61N 1/05* (2013.01); *A61N 1/36157* (2013.01)

(56) References Cited

U.S. PATENT DOCUMENTS

| | | | |
|---|---|---|---|
| 5,540,734 | A | 7/1996 | Zabara |
| 2002/0103454 | A1* | 8/2002 | Sackner ................. A61H 1/001 604/19 |
| 2003/0144709 | A1 | 7/2003 | Zabara et al. |
| 2008/0306355 | A1 | 12/2008 | Walker |
| 2008/0312712 | A1* | 12/2008 | Penner ............... A61N 1/36007 607/40 |
| 2010/0070004 | A1* | 3/2010 | Hlavka ................. A61N 1/3601 607/62 |
| 2010/0241188 | A1* | 9/2010 | Errico .................. A61N 1/3601 607/42 |
| 2012/0172680 | A1* | 7/2012 | Gelfand ............... A61N 1/3627 600/301 |
| 2012/0296389 | A1 | 11/2012 | Fang |
| 2012/0303098 | A1 | 11/2012 | Perryman |
| 2013/0190645 | A1 | 7/2013 | Wenzel et al. |
| 2013/0237948 | A1* | 9/2013 | Donders ............ A61N 1/36167 604/500 |
| 2013/0303876 | A1 | 11/2013 | Gelfand et al. |
| 2014/0018788 | A1 | 1/2014 | Engelman et al. |
| 2014/0067003 | A1 | 3/2014 | Vase |
| 2015/0202444 | A1* | 7/2015 | Franke ................. A61N 1/3611 607/44 |

FOREIGN PATENT DOCUMENTS

| | | |
|---|---|---|
| WO | 2012092364 A2 | 7/2012 |
| WO | WO 2012/159002 A2 | 11/2012 |
| WO | 2015/109015 A1 | 7/2015 |

OTHER PUBLICATIONS

Sarr et. al, "The Empower Study: Randomized, Prospective, Double-Blind, Multicenter Trial of Vagal Blockade to Induce Weight Loss in Morbid Obesity", Obesity Surgery, vol. 22, No. 11, 2012, pp. 1771 -1782.

Donoghue, et al., *Post-Synaptic Activity Evoked in the Nucleus Tractus Solitarus By Carotid Sinus and Aortic Nerve Afferents In The Cat*, J. Physiology, 360:261-273 (1985).

Jianping Weng, et al. "Standards of Care for Type 2 Diabetes in China". Diabetes/Metabolism Research and Reviews, 32: 442-458 (2016).

* cited by examiner

A

B

A.

B.

|  | Before diet | 14 weeks of diet | 25 weeks of diet |
|---|---|---|---|
| Baseline | 0.0 | 0.0 | 0.0 |
| Total Area | 20908 | 25026 | 23693 |
| Total Peak Area | 20908 | 25026 | 23693 |
| Number of Peaks | 1.000 | 1.000 | 1.000 |

A) HF diet - Basal and response to 0%O$_2$

B) Control - Basal and response to 0%O$_2$

C) HF diet - Basal and response to 5%O$_2$

D) Control - Basal and response to 5%O$_2$

A

B

A

B

C

NEUROMODULATION DEVICE AND METHOD FOR TREATING METABOLIC DISORDERS

This application is filed pursuant to 35 U.S.C. § 371 as a U.S. National Phase Application of International patent application Ser. No. PCT/PT2015/000047 filed Nov. 3, 2015, which claims priority to U.S. Provisional Application Ser. No. 62/074,136 filed Nov. 3, 2014, and the entire contents of each of the foregoing applications a hereby incorporated by reference.

TECHNICAL FIELD

This invention relates to medical devices and, more particularly to medical devices that deliver neuromodulating therapy.

BACKGROUND

The rapid increase in prevalence of metabolic disorders such as type 2 diabetes mellitus (T2D, or T2DM), obesity, impaired glucose tolerance (where patients go on to develop T2DM if left untreated) constitutes a severe unmet medical need. Currently available treatments for these disorders are insufficient to control the disease in a significant number of patients, and often produce unwanted side effects.

The carotid bodies (CB) are peripheral chemoreceptors that sense changes in arterial blood $O_2$, $CO_2$ and pH levels. Hypoxia, hypercapnia and acidosis are known to activate the CB. Upon sensing changes, the CB modulates the neural activity (i.e. the action potential pattern and frequency) in their sensory nerve, the carotid sinus nerve (CSN). CSN activity is interpreted by the elements of the brain stem that control efferent reflexes including normalization of blood gases via hyperventilation, and the regulation of blood pressure and cardiac performance via sympathetic nervous system (SNS) activation. Consistent with this notion, CB de-afferentation through carotid sinus nerve denervation reduces the overactive sympathetic activity in spontaneously hypertensive rats (McBryde et al, *Nat Commun.* 2013; 4:2395).

Recently, the carotid body have been implicated in the control of energy homeostasis and regulation of whole body insulin sensitivity (Riberio et al. (2013) *Diabetes.* 62: 2905-16, Limberg *Med Hypotheses.* 2014 June; 82(6):730-5). Riberio et al. (supra) demonstrated that healthy animals fed a high fat or high sugar diet develop insulin resistance and hypertension, but that if healthy rats undergo carotid sinus nerve (CSN) resection prior to beginning the diet, the development of insulin resistance and hypertension is prevented. However these procedures were performed on otherwise healthy animal that do not carry any of the associated symptoms or pathologies of metabolic disorders known to affect the metabolic system and perpetuate disease. No data are available from animals more representative of an active disease state.

SUMMARY

Using animal models representative of both established type 2 diabetes and developing type 2 diabetes ("prediabetes"), each characterised by insulin resistance and an impaired response to glucose, it is demonstrated herein that modulation of neural activity in the CSN can treat conditions associated with impaired glucose control. In particular, in rats exhibiting a disease state comparable to type 2 diabetes as well as in those exhibiting a disease state comparable to prediabetes, modulating CSN neural activity restores insulin sensitivity, and also reduces the rate of weight gain and fat accumulation (FIGS. 5-7 for T2D and Table 1 for prediabetes). In the model of T2D, inhibiting CSN neural activity improves glucose tolerance and insulin sensitivity back towards normal levels (FIGS. 8-10 and FIGS. 20 and 21). These effects in turn will have beneficial effects on other conditions associated with impaired control of glucose and responses to insulin, as well as those conditions associated with increased weight and fat levels, for example obesity and hypertension.

It is further demonstrated herein that in animals in a prediabetic state, the neural activity in the CSN is notably different to the neural activity in healthy animals both at baseline and upon sensory changes, particularly the frequency and amplitude of aggregate action potentials (FIG. 11). This indicates that a type 2 diabetes-like disease state is closely associated with a change in neural activity in the CSN. This abnormal neural activity associated with the disease state can therefore be modulated in order to provide an effective treatment for the conditions associated with impaired glucose control and/or insulin resistance. Further, abnormal neural activity can be a measure of the disease state and may be used in closed loop to control the modulation—for example, detection of abnormal neural activity in the CSN can indicate a disease state, and thereby determine the type and level of modulation of CSN neural activity to treat that disease state. Modulation of the neural activity will provide a subtle and versatile mode of treatment without necessarily requiring removal of the CSN. Pox example, it will allow the titration of treatment in response to disease progression and treatment response. The modulation could also achieve a therapeutic effect whilst maintaining function for other physiological aspects of the CSN and carotid body, such as the ability to detect changes in blood gases and thereby ensuring an adequate physiological response to exercise. It is clear that adversely affecting such aspects is not desired in an effective treatment paradigm of metabolic disorders.

Therefore, in a first aspect is provided a device for inhibiting the neural activity of a carotid sinus nerve (CSN) or carotid body of a subject, the device comprising one or more transducers configured to apply a signal to the CSN or associated carotid body of the subject, optionally at least two such transducers; and a controller coupled to the one or more transducers, the controller controlling the signal to be applied by the one or more transducers, such that the signal inhibits the neural activity of the CSN or carotid body to produce a physiological response in the subject, wherein the physiological response is one or more of the group consisting of: an increase in insulin sensitivity in the subject, an increase in glucose tolerance in the subject, a decrease in (fasting) plasma glucose concentration in the subject, a reduction in subcutaneous fat content in the subject, and a reduction in obesity in the subject.

In another aspect is provided a method of treating a condition associated with impaired glucose control in a subject comprising implanting in the subject a device according to the first aspect, positioning at least one transducer of the apparatus in signalling contact with a CSN or carotid body of the subject and activating the apparatus.

In another aspect is provided a method of inhibiting neural signalling in the CSN of a subject comprising implanting in the subject a device according to the first aspect, positioning at least one transducer of the apparatus in signalling contact with a CSN or carotid body of the subject, and activating the apparatus.

In a further aspect is provided a method of treating a condition associated with impaired glucose control in a subject, the method comprising applying a signal to a part or all of a carotid sinus nerve (CSN) and/or a carotid body of said subject to inhibit the neural activity of a CSN in the subject.

In a further aspect is provided a neuromodulatory electrical waveform for use in treating insulin resistance in a subject, wherein the waveform is a kiloHertz alternating current (AC) waveform having a frequency of 1 to 50 KHz, such that, when applied to a carotid sinus nerve (CSN) of the subject, the waveform inhibits neural signalling in the CSN.

In a further aspect is provided use of a neuromodulation device for treating a condition associated with impaired glucose control in a subject such as insulin resistance, by modulating afferent neural activity in a carotid sinus nerve of the subject.

SUMMARY OF THE DRAWINGS

FIG. 1: Example implementations of device including one or more neuromodulation devices for carrying out the invention.

DETAILED DESCRIPTION

Figure 1A:
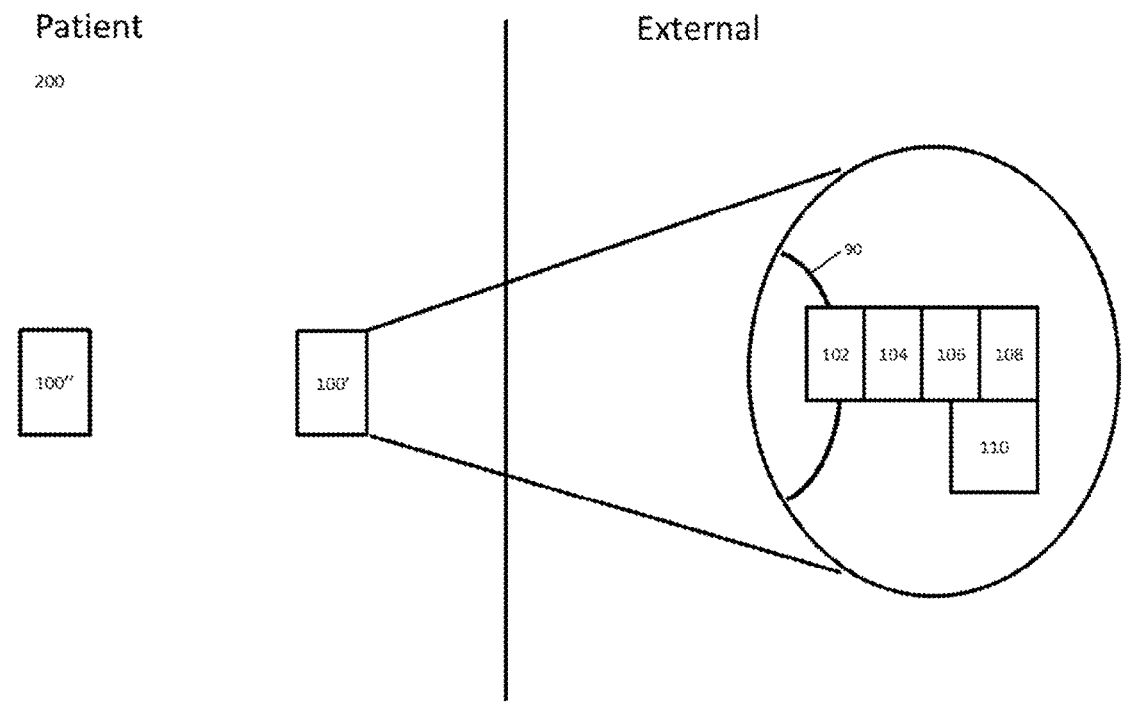
FIGS. 1A: Shows schematically components of one of the neuromodulation devices.

The terms as used herein are given their conventional definition in the art as understood by the skilled person, unless otherwise defined below. In the case of any inconsistency or doubt, the definition as provided herein should take precedence.

As used herein, application of a signal may equate to the transfer of energy in a suitable form to carry out the intended effect of the signal. That is, application of a signal to a carotid sinus nerve or carotid body may equate to the transfer of energy to (or from) the carotid sinus nerve or carotid body (as appropriate) to carry out the intended effect. For example, the energy transferred may be electrical, mechanical (including acoustic, such as ultrasound), electromagnetic (e.g. optical), magnetic or thermal energy. It is noted that application of a signal as used herein does not include a pharmaceutical intervention.

As used herein, a "non-destructive signal" is a signal as defined above that, when applied, does not irreversibly damage the underlying neural signal conduction ability of the nerve. That is, application of a non-destructive signal maintains the ability of the CSN (or fibres thereof, or other nerve tissue to which the signal is applied) to conduct action potentials when application of the signal ceases, even if that conduction is in practice inhibited or blocked as a result of application of the non-destructive signal.

As used herein, an "impaired glucose control" is taken to mean an inability to maintain blood glucose levels at a normal level (i.e. within normal limits for a healthy individual). As will be appreciated by the skilled person, this will vary based on the type of subject and can be determined by a number of methods well known in the art, for example a glucose tolerance test (GTT). For example, in humans undergoing an oral glucose tolerance test, a glucose level at 2 hours of less than or equal to 7.8 mmol/L is considered normal. A glucose level at 2 hours of more than 7.8 mmol/L is indicative of impaired glucose control.

As used herein, "insulin resistance" is given its normal meaning in the art—i.e. in subject or patient exhibiting insulin resistance, the physiological response to insulin in the subject or patient is refractory, such that a higher level of insulin is required in order to control blood glucose levels, compared to the insulin level required in a healthy individual. Insulin sensitivity is used herein as the reciprocal to insulin resistance—that is, an increase in insulin sensitivity equates to a decrease in insulin resistance, and vice versa. Insulin resistance may be determined using any method known in the art, for example a GTT, a hyperinsulinaemic clamp or an insulin suppression test.

Conditions associated with impaired glucose control include those conditions thought to cause the impairment (for example insulin resistance, obesity, metabolic syndrome, Type I diabetes, Hepatitis C infection, acromegaly) and conditions resulting from the impairment (for example obesity, sleep apnoea syndrome, dyslipidaemia, hypertension, Type II diabetes). It will be appreciated that some conditions can be both a cause of and caused by impaired glucose control. Other conditions associated with impaired with glucose control would be appreciated by the skilled person. It will also be appreciated that these conditions may also be associated with insulin resistance.

As used herein, the carotid sinus nerve (CSN) is taken to mean the afferent branch of the glossopharyngeal nerve carrying neural signals from the carotid body to the brain. It includes both the chemoreceptor branch and the baroreceptor branch of the CSN, as well as the trunk of the nerve that carries the nerve fibres from the two aforementioned branches (the carotid sinus nerve is also known as the nerve of Hering or Hering's nerve).

As used herein, "neural activity" of a nerve is taken to mean the signalling activity of the nerve, for example the amplitude, frequency and/or pattern of action potentials in the nerve. The term "pattern", as used herein in the context of action potentials in the nerve, is intended to include one or more of: local field potential(s), compound action potential(s), aggregate action potential(s), and also magnitudes, frequencies, areas under the curve and other patterns of action potentials in the nerve or sub-groups (e.g. fascicules) of neurons therein.

Modulation of neural activity, as used herein, is taken to mean that the signalling activity of the nerve is altered from the baseline neural activity—that is, the signalling activity of the nerve in the subject prior to any intervention. Such modulation may inhibit, block, or otherwise change the neural activity compared to baseline activity.

Where the modulation of neural activity is inhibition of neural activity, such inhibition may be partial inhibition. Partial inhibition may be such that the total signalling activity of the whole nerve is partially reduced, or that the total signalling activity of a subset of nerve fibres of the nerve is fully reduced (i.e. there is no neural activity in that subset of fibres of the nerve), or that the total signalling of a subset of nerve fibres of the nerve is partially reduced compared to baseline neural activity in that subset of fibres of the nerve. Where the modulation of neural activity is inhibition of neural activity, this also encompasses full inhibition of neural activity in the nerve—that is, there is no neural activity in the whole nerve.

In some cases, the inhibition of neural activity may be a block of neural activity. Where modulation of neural activity is a block on neural activity, such blocking may be a partial block, for example a reduction in neural activity of 5%, 10%, 15%, 20%, 25%, 30%, 35%, 40%, 45%, 40%, 50%, 60%, 70%, 80%, 90% or 95%, or blocking of neural activity in a subset of nerve fibres of the nerve. Alternatively, such blocking may be a full block—i.e. blocking of neural activity in the whole nerve. A block on neural activity is understood to be blocking neural activity from continuing past the point of the block. That is, when the block is applied, action potentials may travel along the nerve or subset of nerve fibres to the point of the block, but not beyond the point of the block.

Modulation of neural activity may also be an alteration in the pattern of action potentials. It will be appreciated that the pattern of action potentials can be modulated without necessarily changing the overall frequency or amplitude. For example, modulation of the neural activity may be such that the pattern of action potentials is altered to more closely resemble a healthy state rather than a disease state.

Modulation of neural activity may comprise altering the neural activity in various other ways, for example increasing or inhibiting a particular part of the neural activity and/or stimulating new elements of activity, for example in particular intervals of time, in particular frequency bands, according to particular patterns and so forth. Such altering of neural activity may for example represent both Increases and/or decreases with respect to the baseline activity.

Modulation of the neural activity may be temporary. As used herein, "temporary" is used interchangeably with "reversible", each being taken to mean that the modulated neural activity (whether that is an inhibition, block or other modulation of neural activity or change in pattern versus baseline activity) is not permanent. That is, upon cessation of the signal, neural activity in the nerve returns substantially towards baseline neural activity within 1-60 seconds, or within 1-60 minutes, or within 1-24 hours, optionally 1-12 hours, optionally 1-6 hours, optionally 1-4 hours, optionally 1-2 hours, or within 1-7 days, optionally 1-4 days, optionally 1-2 days. In some instances of temporary modulation, the neural activity returns substantially fully to baseline neural activity. That is, the neural activity following cessation of the signal is substantially the same as the neural activity prior to the signal being applied—i.e. prior to modulation.

Modulation of the neural activity may be persistent. As used herein, "persistent" is taken to mean that the modulated neural activity (whether that is an inhibition, block or other modulation of neural activity or change in pattern versus baseline activity) has a prolonged effect. That is, upon cessation of the signal, neural activity in the nerve remains substantially the same as when the signal was being applied—i.e. the neural activity during and following modulation is substantially the same Modulation of the neural activity may be corrective. As used herein, "corrective" is taken to mean that the modulated neural activity (whether that is an inhibition, block or other modulation of neural activity or change in pattern versus baseline activity) alters the neural activity towards the pattern of neural activity in a healthy individual. That is, upon cessation of the signal, neural activity in the nerve more closely resembles the pattern of action potentials in the CSN observed in a healthy subject than prior to modulation, preferably substantially fully resembles the pattern of action potentials in the CSN observed in a healthy subject. Such corrective modulation caused by the signal can be any modulation as defined herein. For example, application of the signal may result in a block on neural activity, and upon cessation of the signal, the pattern of action potentials in the nerve resembles the pattern of action potentials observed in a healthy subject. By way of further example, application of the signal may result in modulation such that the neural activity resembles the pattern of action potentials observed in a healthy subject, and upon cessation of the signal, the pattern of action potentials in the nerve remains the pattern of action potentials observed in a healthy subject.

As used herein, an "improvement in a measurable physiological parameter" is taken to mean that for any given physiological parameter, an improvement is a change in the value of that parameter in the subject towards the normal value or normal range for that value—i.e. towards the expected value in a healthy individual.

For an example, in a subject having a condition associated with impaired glucose control, or having insulin resistance, an improvement in a measurable parameter may be: a reduction in sympathetic tone, an increase in insulin sensitivity, an increase in glucose tolerance, a reduction in total fat mass, a reduction in visceral fat mass, a reduction in subcutaneous fat mass, reduction in plasma catecholamines, reduction in urinary metanephrines, and a reduction in glycated haemoglobin (HbA1c), a reduction in circulating triglycerides, assuming the subject is exhibiting abnormal values for the respective parameter.

The physiological effect may be temporary. That is, upon cessation of the signal, the measured physiological parameter in which an improvement was induced by the signal returns substantially towards baseline neural activity within 1-60 seconds, or within 1-60 minutes, or within 1-24 hours, optionally 1-12 hours, optionally 1-6 hours, optionally 1-4 hours, optionally 1-2 hours, or within 1-7 days, optionally 1-4 days, optionally 1-2 days. In some instances, the physiological parameter returns substantially fully to baseline neural activity. That is, the value of the physiological parameter following cessation of the signal is substantially the same as the value for the physiological parameter prior to the signal being applied—i.e. prior to modulation.

The physiological effect may be persistent. That is, upon cessation of the signal, the value of the measurable physiological parameter remains substantially the same as when the signal was being applied—i.e. the value for the physiological parameter during and following modulation is substantially the same The physiological effect may be corrective. That is, upon cessation of the signal, the value of the measurable physiological parameter more closely resembles the value for that parameter observed in a healthy subject than prior to modulation, preferably substantially fully resembles the value for that parameter observed in a healthy subject.

As used herein, a physiological parameter is not affected by modulation of the neural activity it the parameter does not change as a result of the modulation from the average value of that parameter exhibited by the subject or subject when no intervention has been performed—i.e. it does not depart from the baseline value for that parameter.

The skilled person will appreciate that the baseline for any neural activity or physiological parameter in an individual need not be a fixed or specific value, but rather can fluctuate within a normal range or may be an average value with associated error and confidence intervals. Suitable methods for determining baseline values would be well known to the skilled person.

As used herein, a measurable physiological parameter is detected in a subject when the value for that parameter exhibited by the subject at the time of detection is determined. A detector is any element able to make such a determination.

A "predefined threshold value" for a physiological parameter is the minimum (or maximum) value for that parameter that must be exhibited by a subject or subject before the specified intervention is applied. For any given parameter, the threshold value may be defined as a value indicative of a pathological state or a disease state (e.g. sympathetic tone (neural, hemodynamic (e.g. heart rate, blood pressure, heart rate variability) or circulating plasma/urine biomarkers) greater than a threshold sympathetic tone, or greater than a sympathetic tone in a healthy individual, blood insulin levels greater than healthy levels, CSN signalling exhibiting a certain activity level or pattern). Alternatively, the threshold value may be defined as a value indicative of a physiological state of the subject (that the subject is, for example, asleep, post-prandial, or exercising). Appropriate values for any given parameter would be simply determined by the skilled person (for example, with reference to medical standards of practice).

Such a threshold value for a given physiological parameter is exceeded if the value exhibited by the subject is beyond the threshold value—that is, the exhibited value is a greater departure from the normal or healthy value for that parameter than the predefined threshold value.

A "neuromodulation device" or "neuromodulation apparatus" as used herein is a device configured to modulate the neural activity of a nerve. Neuromodulation devices or apparatuses as described herein can be comprised of one or more parts. The neuromodulation devices or apparatuses comprise at least one transducer capable of effectively applying a signal to a nerve. In those embodiments in which the neuromodulation device is at least partially implanted in the subject, the elements of the device that are to be implanted in the subject are constructed such that they are suitable for such implantation. Such suitable constructions would be well known to the skilled person.

Various exemplary fully implantable neuromodulation devices are currently available, such as the vagus nerve stimulator of SetPoint Medical, in clinical development for the treatment of rheumatoid arthritis (*Arthritis & Rheumatism*, Volume 64, No. 10 (Supplement), page S195 (Abstract No. 451), October 2012. *"Pilot study of stimulation of the Cholinergic Anti-Inflammatory Pathway with an Implantable Vagus Nerve Stimulation Device in Patients with Rheumatoid Arthritis"*, Prieda A. Koopman et al), and the INTERSTIM™ device (Medtronic, Inc.), a fully implantable device utilised for sacral nerve modulation in the treatment of overactive bladder.

Suitable neuromodulation devices can be fabricated with characteristics as described herein, for example for implantation within the nerve (e.g. intrafascicularly), for partially or wholly surrounding the nerve (e.g. a cuff interface with the nerve).

As used herein, "implanted" is taken to mean positioned within the subject's body. Partial implantation means that only part of the device is implanted—i.e. only part of the device is positioned within the subject's body, with other elements of the device external to the subject's body. For example, the transducer and controller of the device may be wholly implanted within the subject, and an input element may be external to the subject's body. Wholly implanted means that the entire of the device is positioned within the subject's body.

As used herein, "charge-balanced" in relation to a DC current is taken to mean that the positive or negative charge introduced into any system (e.g. a nerve) as a result of a DC current being applied is balanced by the introduction of the opposite charge in order to achieve overall (net) neutrality.

Figure 11:
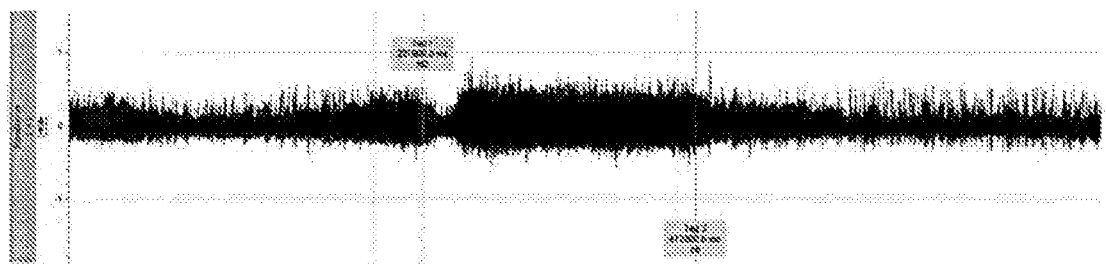
FIG. 11: Representative (of 6 animals) recordings of carotid sinus nerve activity in basal conditions and evoked by hypoxia in an animal model of prediabetes (rat fed HF diet for 3 weeks) and in a control rat. A) and B): recordings of CSN chemosensory activity in basal conditions and evoked by 0% $O_2$ in a HF rat (A) and control rat (B); C) and D): recordings of CSN chemosensory activity in basal conditions and evoked by 5% $O_2$ in a HF (A) and control (B) rat.
Figure 11:
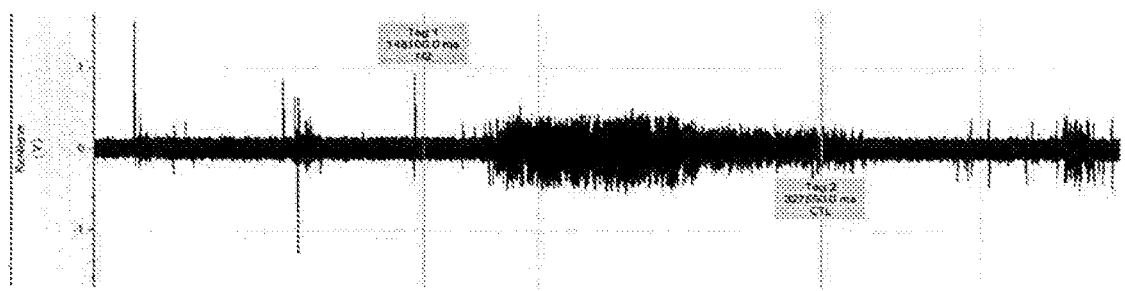
Figure 11:
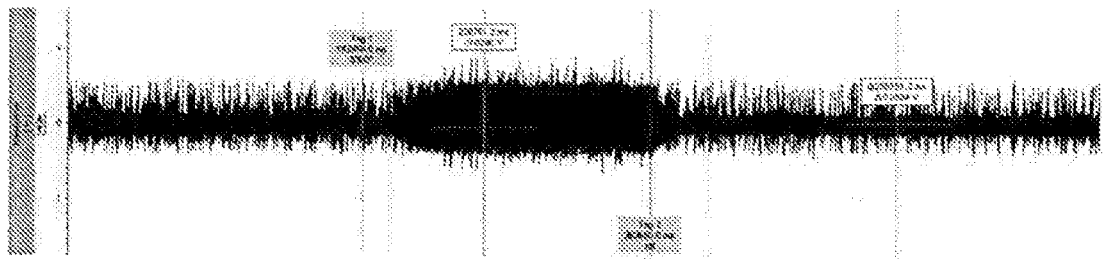
Figure 11:
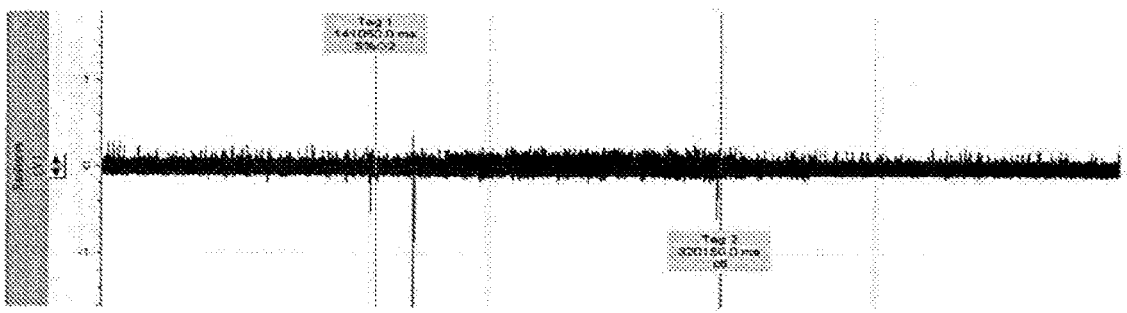

The carotid bodies (CB) are peripheral chemoreceptors that classically respond to hypoxia by increasing chemosensory activity in the carotid sinus nerve (CSN), causing hyperventilation and activation of the sympathoadrenal system. Besides its role in the control of ventilation, the CB has been proposed as a metabolic sensor implicated in the control of energy homeostasis. Recently, the inventors have described that the carotid bodies may also be involved in the etiology of insulin resistance, core metabolic and haemodynamic disturbances of highly prevalent diseases like prediabetes, type 2 diabetes, and obstructive sleep apnoea (Ribeiro et al., 2013, which is incorporated herein by reference). In this study, CSN resection in healthy rats prevented the development of insulin resistance and hypertension induced by subsequent hypercaloric diets. CSN resection prior to hypercaloric diet also reduced weight gain and avoided visceral fat deposition in this model. Herein it is demonstrated that CB overactivation and increased CSN signalling is associated with the pathogenesis of metabolic and hemodynamic disturbances. As demonstrated in the present application, carotid sinus nerve (CSN) activity is increased in animal models of insulin resistance (FIG. 11). Therefore modulation of the neural activity in the CSN will result in treatment of conditions associated with such an impaired glucose control in a subject. Further, abolishment of CB activity by hyperoxia ameliorates glucose tolerance in type 2 diabetes patients (Vera-Cruz, Guerreiro, Ribeiro, Guarino and Conde [in print], Advances in Experimental Medicine and Biology: Arterial Chemoreceptors in Physiology and Pathophysiology: Hyperbaric oxygen therapy improves glucose homeostasis in type 2 diabetes subjects: a likely involvement of the carotid bodies, incorporated herein by reference).

Therefore, in accordance with a first aspect of the invention there is provided an device for inhibiting the neural activity of a carotid sinus nerve (CSN) of a subject, the device comprising: one or more transducers configured to apply a signal to the CSN or associated carotid body of the subject, optionally at least two such transducers; and a controller coupled to the transducer or transducers, the controller controlling the signal to be applied by the one or more transducers, such that the signal modulates the neural activity of the CSN to produce a physiological response in the subject, wherein the physiological response produced in the subject is one or more of the group consisting of: reduction in sympathetic tone, increase in insulin sensitivity, decrease in insulin resistance, increase in glucose tolerance, a reduction in visceral fat mass, a reduction in subcutaneous fat mass, reduction in plasma catecholamines, reduction in tissue catecholamines, reduction in urinary metanephrines, a reduction in glycated haemoglobin (HbA1c) or a reduction in circulating triglycerides. Preferably the physiological response is one or more of, more preferably all of, increase in insulin sensitivity, decrease in insulin resistance, and increase in glucose tolerance.

In certain embodiments, the signal applied by the one or more transducers is a non-destructive signal.

In certain such embodiments, the signal applied by the one or more transducers is an electrical signal, an electromagnetic signal, an optical signal, an ultrasonic signal, or a thermal signal. In those embodiments in which the device has at least two transducers, the signal which each of the transducers is configured to apply is independently selected from an electrical signal, an optical signal, an ultrasonic signal, and a thermal signal. That is, each transducer may be configured to apply a different signal. Alternatively, in certain embodiments each transducer is configured to apply the same signal.

In certain embodiments, each of the one or more transducers may be comprised of one or more electrodes, one or more photon sources, one or more ultrasound transducers, one more sources of heat, or one or more other types of transducer arranged to put the signal into effect.

In certain embodiments, the signal applied by the one or more transducers is an electrical signal, for example a voltage or current. In certain such embodiments the signal applied comprises a direct current (DC), such as a charge balanced direct current, or an alternating current (AC) waveform, or both a DC and an AC waveform.

In certain embodiments the electrical signal applied by the one or more transducers has a frequency of 0.5 to 100 kHz, optionally 1 to 50 kHz, optionally 5 to 50 KHz. In certain embodiments the signal has a frequency of 25 to 55 kHz, optionally 30-50 kHz. In certain embodiments, the signal has a frequency of 5-10 KHz. In certain embodiments, the electrical signal has a frequency of greater than 1 kHz. It is shown herein that electrical signals having a frequency of more than 20 kHz are particularly effective at inhibiting (in particular, blocking) neural activity of the CSN. Therefore, in certain preferred embodiments the electrical signal has a frequency greater than 20 kHz, optionally at least 25 kHz, optionally at least 30 kHz. In certain embodiments the signal has a frequency of 30 kHz, 40 kHz or 50 kHz.

In certain embodiments, an onset response as a result of the signal being applied can be avoided if the signal does not have a frequency of 20 kHz or lower, for example 1-20 kHz, or 1-10 KHz.

In certain embodiments the DC waveform or AC waveform may be a square, sinusoidal, triangular or complex waveform. The DC waveform may alternatively be a constant amplitude waveform. In certain embodiments the electrical signal is an AC sinusoidal waveform.

It will be appreciated by the skilled person that the current amplitude of an applied electrical signal necessary to achieve the intended neuromodulation will depend upon the positioning of the electrode and the associated electrophysiological characteristics (e.g. impedance). It is within the ability of the skilled person to determine the appropriate current amplitude for achieving the intended neuromodulation in a given subject. For example, the skilled person is aware of methods suitable to monitor the neural activity profile induced by neuromodulation.

In certain embodiments, the electrical signal has a current of 0.5-5 mA, optionally 0.5 mA-2 mA, optionally 0.5-1.5 mA, optionally 1 mA or 2 mA.

In certain embodiments, the signal is an electrical signal comprising an AC sinusoidal waveform having a frequency of greater than 25 kHz, optionally 30-50 kHz. In certain such embodiments, the signal is an electrical signal comprising an AC sinusoidal waveform having a frequency of greater than 25 kHz, optionally 30-50 kHz having a current of 1 mA or 2 mA.

In those embodiments in which the signal applied by the one or more transducers is an electrical signal, at least one of the one or more transducers is an electrode configured to apply the electrical signal. In certain such embodiments, all the transducers are electrodes configured to apply an electrical signal, optionally the same electrical signal.

In those embodiments wherein the signal is an electrical signal and each transducer configured to apply the signal is an electrode, the electrode may be a bipolar electrode, or a tripolar electrode. The electrode may be a cuff electrode or a wire electrode.

In certain embodiments wherein the signal applied by the one or more transducers is a thermal signal, the signal reduces the temperature of the nerve (i.e. cools the nerve). In certain such embodiments the nerve is cooled to 14° C. or lower to partially inhibit neural activity, or to 6° C. or lower, for example 2° C., to fully inhibit neural activity. In such embodiments, it is preferably not to cause damage to the nerve. In certain alternative embodiments, the signal increases the temperature of the nerve (i.e. heats the nerve). In certain embodiments, neural activity is inhibited by increasing the nerve by at least 5° C., for example by 5° C., 6° C., 7° C., 8° C. In certain embodiments, the signal both heats and cools the nerve, simultaneously at different locations on the nerve, or sequentially at the same or different location on the nerve.

In those embodiments in which the signal applied by the one or more transducers is a thermal signal, at least one of the one or more transducers is a transducer configured to apply a thermal signal. In certain such embodiments, all the transducers are configured to apply a thermal signal, optionally the same thermal signal.

In certain embodiments, one or more of the one or more transducers comprise a Peltier element configured to apply a thermal signal, optionally all of the one or more transducers comprise a Peltier element. In certain embodiments, one or more of the one or more transducers comprise a laser diode configured to apply a thermal signal, optionally all of the one or more transducers comprise a laser diode configured to apply a thermal, signal. In certain embodiments, one or more of the one or more transducers comprise a electrically resistive element configured to apply a thermal signal, optionally all of the one or more transducers comprise a electrically resistive element configured to apply a thermal signal.

In certain embodiments the signal applied by the one or more transducers is a mechanical signal. In certain embodiments, the mechanical signal is a pressure signal. In certain such embodiments, the transducer causes a pressure of at least 250 mmHg to be applied to the nerve, thereby inhibiting neural activity. In certain alternative embodiments, the signal is an ultrasonic signal. In certain such embodiments, the ultrasonic signal has a frequency of 0.5-2.0 MHz, optionally 0.5-1.5 MHz, optionally 1.1 MHz. In certain embodiments, the ultrasonic signal has a density of 10-100 W/cm$^2$, for example 13.6 W/cm$^2$ or 93 W/cm$^2$.

In certain embodiments the signal applied by the one or more transducers is an electromagnetic signal, optionally an optical signal. In certain such embodiments, the one or more transducers comprise a laser and/or a light emitting diode configured to apply the optical signal. In certain such embodiments, the optical signal (for example the laser signal) has an energy density from 500 mW/cm$^2$ to 900 W/cm$^2$. In certain alternative embodiments, the signal is a magnetic signal. In certain such embodiments, the magnetic signal is a biphasic signal with a frequency of 5-15 Hz, optionally 10 Hz. In certain such embodiments, the signal has a pulse duration of 1-1000 µS, for example 500 µS.

In certain embodiments, the physiological response may be temporary. That is, upon cessation of the signal, the measured physiological parameter in which an improvement was induced by the signal returns substantially towards baseline neural activity within 1-60 seconds, or within 1-60 minutes, or within 1-24 hours, optionally 1-12 hours, optionally 1-6 hours, optionally 1-4 hours, optionally 1-2 hours, or within 1-7 days, optionally 1-4 days, optionally 1-2 days. In some instances, the physiological parameter returns substantially fully to baseline neural activity. That is, the value of the physiological parameter following cessation of the signal is substantially the same as the value for the physiological parameter prior to the signal being applied—i.e. prior to modulation.

In certain embodiments, the physiological response may be persistent. That is, upon cessation of the signal, the value of the measurable physiological parameter remains substantially the same as when the signal was being applied—i.e. the value for the physiological parameter during and following modulation is substantially the same In certain embodiments, the physiological response may be corrective. That is, upon cessation of the signal, the value of the measurable physiological parameter more closely resembles the value for that parameter observed in a healthy subject than prior to modulation, preferably substantially fully resembles the value for that parameter observed in a healthy subject.

In certain embodiments, the device further comprises means to detect one or more physiological parameters in the subject. Such a means may be one or more detectors configured to detect the one or more physiological parameters. That is, in such embodiments each detector may detect more than one physiological parameter, for example all the detected physiological parameters. Alternatively, in such embodiments each detector is configured to detect a separate parameter of the one or more physiological parameters detected.

In such certain embodiments, the controller is coupled to the means to detect one or more physiological parameters, and causes the transducer or transducers to apply the signal when the physiological parameter is detected to be meeting or exceeding a predefined threshold value.

In certain embodiments, the one or more detected physiological parameters comprise one or more of the group consisting of: sympathetic tone, plasma insulin concentration, plasma glucose concentration, plasma catecholamine concentration (i.e. one or more of epinephrine, norepinephrine, metanephrine, normetanephrine and dopamine) concentration, tissue catecholamine concentration, plasma HbA1c concentration or plasma triglyceride concentration.

In certain embodiments, the one or more detected physiological parameters comprise an action potential or pattern of action potentials in a nerve of the subject, wherein the action potential or pattern of action potentials is associated with the condition associated with an impaired response to glucose that is to be treated. In certain such embodiments, the nerve is a sympathetic nerve. In certain such embodiments, the nerve is a splanchnic sympathetic nerve. In certain embodiments, the nerve is the peroneal nerve, the sciatic nerve (or one or more branches thereof), or muscle sympathetic nerve terminals. In certain alternative such embodiments, the nerve is an afferent nerve involved in metabolic regulation, for example afferent nerves from the liver or from the GI tract. In one desirable embodiment, the nerve is the CSN. In this embodiment, the detected pattern of action potentials may be associated with impaired response to glucose or insulin.

It will be appreciated that any two or more of the indicated physiological parameters may be detected in parallel or consecutively. For example, in certain embodiments, the controller is coupled to a detector or detectors configured to detect the pattern of action potentials in the CSN at the same time as glucose tolerance in the subject.

The modulation in neural activity as a result of applying the signal is inhibition of neural activity in the CSN. That is, in such embodiments, application of the signal results in the neural activity in at least part of the CSN being reduced compared to the baseline neural activity in that part of the nerve. Such a reduction in activity could equally be across the whole nerve, in which case neural activity would be reduced across the whole nerve. Therefore, in certain such embodiments, a result of applying the signal is at least partial inhibition of neural activity in the CSN. In certain such embodiments a result of applying the signal is at least partial inhibition of neural activity in the chemoreceptor branch of the CSN. In certain such embodiments, a result of applying the signal is full inhibition of neural activity in the chemoreceptor branch of the CSN. In certain embodiments, a result of applying the signal is full inhibition of neural activity in the CSN.

In certain embodiments, the modulation in neural activity as a result of applying the signal is a block on neural activity in the CSN. That is, in such embodiments, the application of the signal blocks action potentials from travelling beyond the point of the block in at least a part of the CSN. In certain such embodiments, the modulation is a partial block. In certain alternative embodiments, the modulation is a full block. In a preferred embodiment, the modulation is a partial or full block of neural activity in the CSN.

In certain embodiments, the modulation in neural activity as a result of applying the signal is an alteration to the pattern of action potentials in the CSN. In certain such embodiments, the neural activity is modulated such that the resultant pattern of action potentials in the CSN resembles the pattern of action potentials in the CSN observed in a healthy subject.

Modulation of neural activity may comprise altering the neural activity in various other ways, for example increasing or inhibiting a particular part of the activity and stimulating new elements of activity, for example in particular intervals of time, in particular frequency bands, according to particular patterns and so forth. Such altering of neural activity may for example represent both increases and/or decreases with respect to the baseline activity.

In certain embodiments of the method, the signal is applied intermittently. In certain such embodiments, the signal is applied continuously for at least 5 days, optionally at least 7 days, before ceasing. That is, for such intermittent application of the signal, the signal is applied continuously for at least 5 days (optionally 7 days), then application ceases for a period (e.g. 1 day, 2 days, 3 days, 1 week, 2 weeks, 1 month) before the signal is again applied continuously for at least 5 days (optionally 7 days).

In certain such embodiments wherein the signal is applied intermittently, the signal is applied for a first time period, then stopped for a second time period, then reapplied for a third time period, then stopped for a fourth time period. In such an embodiment, the first, second, third and fourth periods run sequentially and consecutively. The series of first, second, third and fourth periods amounts to one application cycle. In certain such embodiments, multiple application cycles can run consecutively such that the signal is applied in phases, between which phases no signal is applied.

In such embodiments, the duration of the first, second, third and fourth time periods is independently selected. That is, the duration of each time period may be the same or different to any of the other time periods. In certain such embodiments, the duration of each of the first, second, third and fourth time periods may be any time from 1 second (s) to 10 days (d), 2 s to 7 d, 3 s to 4 d, 5 s to 24 hours (24 h), 30 s to 12 h, 1 min to 12 h, 5 min to 8 h, 5 min to 6 h, 10 min to 6 h, 10 min to 4 h, 30 min to 4 h, 1 h to 4 h. In certain embodiments, the duration of each of the first, second, third and fourth time periods is 5 s, 10 s, 30 s, 60 s, 2 min, 5 min, 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 2 d, 3 d, 4 d, 5 d, 6 d, 7 d.

In certain embodiments wherein the controller causes the signal to be applied intermittently, the signal is applied for a specific amount of time per day. In certain such embodiments, the signal is applied for 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain such embodiments, the signal is applied continuously for the specified amount of time. In certain alternative such embodiments, the signal may be applied discontinuously across the day, provided the total time of application amounts to the specified time.

In certain embodiments wherein the controller causes the signal to be applied intermittently, the signal is applied only when the subject is in a specific state. In certain such embodiments, the controller causes the signal to be applied only when the subject is awake. In certain alternative embodiments, the controller causes the signal to be applied only when the subject is asleep. In certain embodiments, the controller causes the signal to be applied prior to and/or after the ingestion of food. In certain embodiments, the controller causes the signal to be applied prior to and/or after the subject undertakes exercise.

In certain such embodiments, the device further comprises an input means. In such embodiments, the status of the subject (i.e. whether the subject is awake, asleep, pre- or post-eating, or pre- or post-taking exercise) can be input into the device by the subject or by a physician. In alternative embodiments, the device further comprises a detector configured to detect the status of the subject, wherein the signal is applied only when the detector detects that the subject is in the specific state.

In certain alternative embodiments, the controller causes the signal to be continuously applied to the CSN and/or carotid body. It will be appreciated that in embodiments wherein the signal is a series of pulses, gaps between pulses do not mean the signal is not continuously applied. Such continuous application may continue indefinitely, e.g. permanently. Alternatively, the continuous application may be for a minimum period, for example the signal may be continuously applied for at least 5 days, or at least 7 days.

In certain embodiments of the device, the inhibition in neural activity caused by the application of the signal (whether that is an inhibition, block or other modulation of neural activity) is temporary/reversible. That is, upon cessation of the signal, neural activity in the nerve returns substantially towards baseline neural activity within 1-60 seconds, or within 1-60 minutes, or within 1-24 hours, optionally 1-12 hours, optionally 1-6 hours, optionally 1-4 hours, optionally 1-2 hours, or within 1-7 days, optionally 1-4 days, optionally 1-2 days. In certain such embodiments, the neural activity returns substantially fully to baseline neural activity. That is, the neural activity following cessation of the signal is substantially the same as the neural activity prior to the signal being applied—i.e. prior to modulation.

In certain alternative embodiments, the inhibition in neural activity caused by the application of the signal is substantially persistent. That is, upon cessation of the signal, neural activity in the nerve remains substantially the same as when the signal was being applied—i.e. the neural activity during and following modulation is substantially the same.

In certain embodiments, the inhibition in neural activity caused by the application of the signal is partially corrective, preferably substantially corrective. That is, upon cessation of the signal, neural activity in the nerve more closely resembles the pattern of action potentials in the CSN observed in a healthy subject than prior to modulation, preferably substantially fully resembles the pattern of action potentials in the CSN observed in a healthy subject. In such embodiments, the modulation caused by the signal can be any modulation as defined herein. For example, application of the signal may result in a block on neural activity, and upon cessation of the signal, the pattern of action potentials in the nerve resembles the pattern of action potentials observed in a healthy subject. By way of further example, application of the signal may result modulation such that the neural activity resembles the pattern of action potentials observed in a healthy subject, and upon cessation of the signal, the pattern of action potentials in the nerve resembles the pattern of action potentials observed in a healthy subject. It is hypothesised that such a corrective effect is the result of a positive feedback loop—that is, the underlying disease state is treated as result of the claimed methods, and therefore the chemosensory signals along the CSN are not abnormal, and therefore the disease state is not perpetuated by the abnormal CSN neural activity.

In certain embodiments, the device is suitable for at least partial implantation into the subject such that at least a portion of the device sits within the body, preferably in proximity to the CSN or carotid body to which the signal is to be applied. In such embodiments, parts of the device, for example the transducer and the controller, may be suitable to be wholly implanted in the subject such that the signal can be applied to the CSN or carotid body, and other parts of the device may be external to the body, for example an input element or remote charging element. In certain embodiments, the device is suitable to be wholly implanted in the subject.

In certain embodiments, the device further comprises one or more of a power supply element, for example a battery, and/or one or more communication elements.

In a further aspect, the invention provides a method for treating a condition associated with impaired glucose control in a subject, the method comprising implanting a device according to the first aspect, positioning at least one transducer of the device in signalling contact with a CSN and/or carotid body of the subject, and activating the device.

The invention also provides a method of inhibiting neural signalling in the CSN of a subject comprising implanting in the subject a device according to the first aspect, positioning at least one transducer of the apparatus in signalling contact with a CSN or carotid body of the subject and activating the apparatus. In certain embodiments of this method, the inhibition of neural signalling in the CSN improves glucose control in the subject.

In such embodiments, the transducer is in signalling contact with the CSN or carotid body when it is positioned such that the signal can be effectively applied to the CSN or carotid body. The device is activated when the device is in an operating state such that the signal will be applied as determined by the controller.

In certain embodiments of these methods, the method is applied bilaterally. That is, in such embodiments, a first transducer is positioned in signalling contact with the left carotid sinus nerve (CSN) and/or left carotid body of said subject to modulate the neural activity of the left CSN in the subject, and a second transducer is positioned in signalling contact with the right carotid sinus nerve (CSN) and/or right carotid body of said subject to modulate the neural activity of the right CSN in the subject. In certain such embodiments, the first and second transducers are part of one device according to the third aspect. In alternative such embodiments, the first and second transducers are part of separate devices according to the third aspect.

Implementation of all aspects of the invention (as discussed both above and below) will be further appreciated by reference to FIGS. 1A-1C.

Figure 1B:
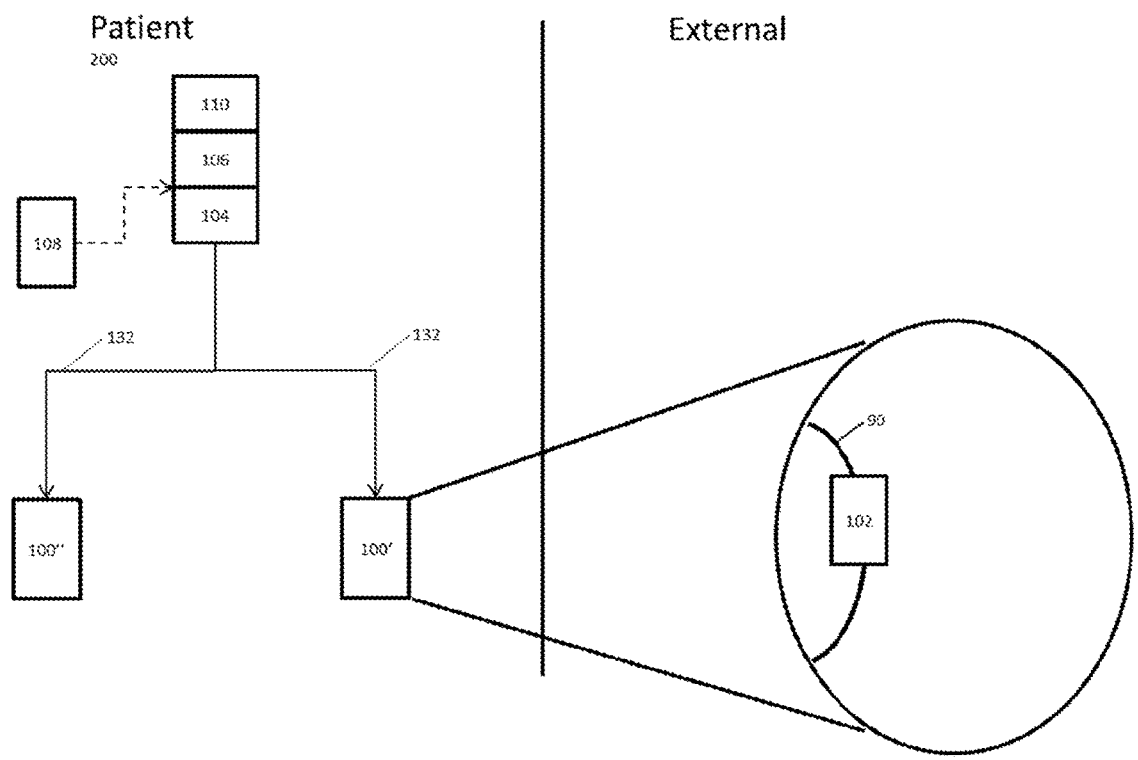
FIGS. 1B: Illustrates some ways in which the device of FIG. 1A may be differently distributed.
Figure 1C:
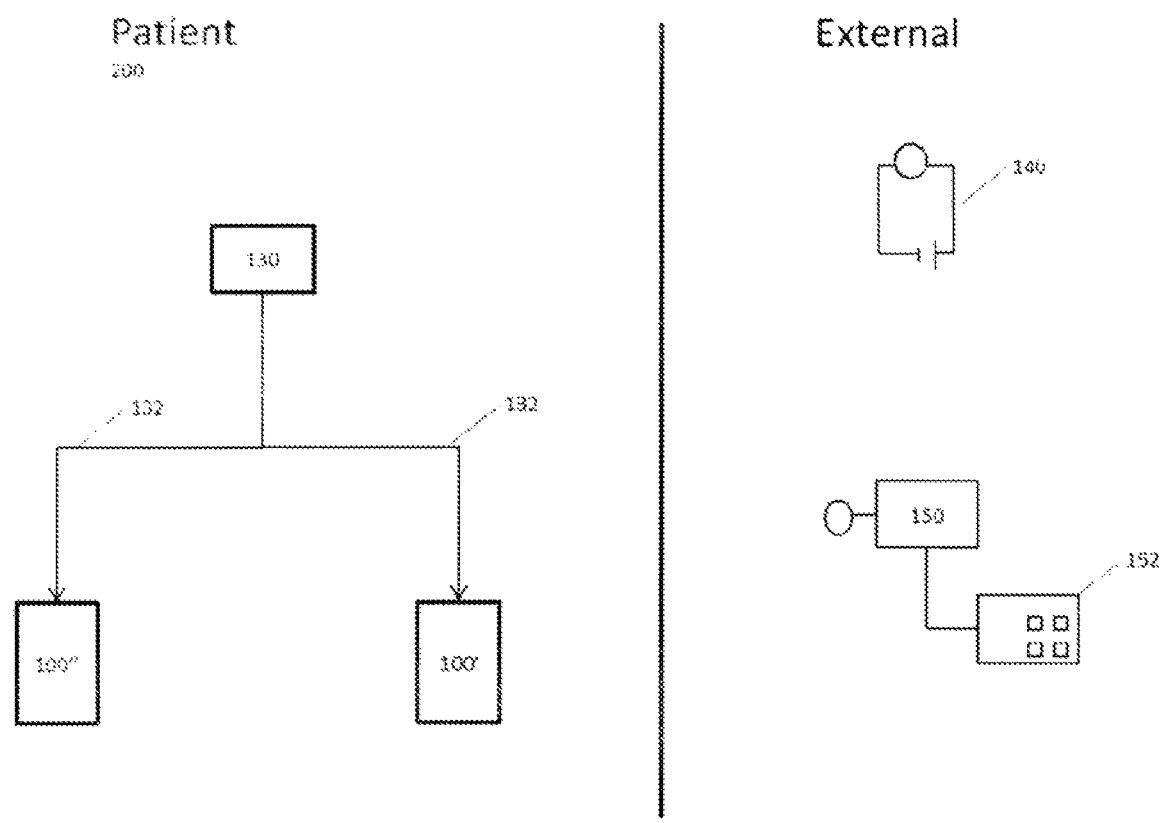
FIGS. 1C: Illustrates some ways in which some functionality of the device of FIG. 1A or 1B is provided not implanted in the subject.

FIGS. 1A-1C show how the invention may be put into effect using one or more neuromodulation devices which are implanted in, located on, or otherwise disposed with respect to a subject 200 in order to carry out any of the various methods described herein. In this way, one or more neuromodulation devices can be used to treat a condition associated with impaired glucose control in a subject, by modulating carotid sinus nerve afferent neural activity.

In each of the FIGS. 1A-1C a separate neuromodulation device 100', 100" is provided in respect of each of the left and right carotid sinus nerves, although as discussed above a device could be provided or used in respect of only one of the left and right nerves. Each such neuromodulation device may be fully or partially implanted in the subject, or otherwise located, so as to provide neuromodulation of the respective carotid sinus nerve, carotid sinus body, or both. FIG. 1A also shows schematically components of one of the neuromodulation devices, in which the device comprises several elements, components or functions grouped together in a single unit and implanted in the subject 200. A first such element is a transducer 102 which is shown in proximity to a carotid sinus nerve 90 of the subject. The transducer 102 may be operated by a controller element 104. The device may comprise one or more further elements such as a communication element 106, a detector element 108, a power supply element 110 and so forth. Each of the left and right neuromodulation devices 100', 100" may operate independently, or may operate in communication with each other, for example using respective communication elements 106.

Each neuromodulation device 100', 100" may carry out the required neuromodulation independently, or in response to one or more control signals. Such a control signal may be provided by the controller 104 according to an algorithm, in response to output of one or more detector elements 108, and/or in response to communications from one or more external sources received using the communications element. As discussed herein, the detector element(s) could be responsive to a variety of different physiological parameters.

FIG. 1B illustrates some ways in which the device of FIG. 1A may be differently distributed. For example, in FIG. 1B the neuromodulation devices 100', 100" comprise transducers 102 implanted proximally to the carotid sinus nerves 90 or bodies, but other elements such as a controller 104, a communication element 106 and a power supply 110 are implemented in a separate control unit 30 which may also be implanted in, or carried by the subject. The control unit 130 then controls the transducers in both of the neuromodulation devices via connections 132 which may for example comprise electrical wires and/or optical fibres for delivering signals and/or power to the transducers.

In the arrangement of FIG. 1B one or more detectors 108 are located separately from the control unit, although one or more such detectors could also or instead be located within the control unit 130 and/or in one or both of the neuromodulation devices 100', 100". The detectors may be used to detect one or more physiological parameters of the subject, and the controller element or control unit then causes the transducers to apply the signal in response to the detected parameter(s), for example only when a detected physiological parameter meets or exceeds a predefined threshold value. Physiological parameters which could be detected for such purposes include sympathetic tone, plasma insulin concentration, insulin sensitivity, plasma glucose concentration, glucose tolerance, plasma catecholamine concentration, tissue catecholamine concentration, plasma HbA1c concentration and plasma triglyceride concentration. Similarly, a detected physiological parameter could be an action potential or pattern of action potentials in a nerve of the subject, for example an efferent or more particularly a sympathetic nerve, wherein the action potential or pattern of action potentials is associated with the condition to be treated. It is demonstrated herein that neural activity in the CSN is increased in animals in a prediabetic state, and thus, in one embodiment, the or each detector 108 may be located on or proximal to the CSN, such as to detect the action potential or pattern of action potentials in the CSN, as indicative of a disease state. In one embodiment, detector 108 may be implanted unilaterally on or proximal to one (i.e. left or right) of the CSN (or, analogously, the CS, or the branch of the glossopharyngeal nerve to the CSN/CB, or the chemosensory branch of the CSN), and the or each transducer 102 may be implanted on or proximally to the other of the CSN (or analogous nerves).

A variety of other ways in which the various functional elements could be located and grouped into the neuromodulation devices, a control unit 130 and elsewhere are of course possible. For example, one or more sensors of FIG. 1B could be used in the arrangement of FIG. 1A or 1C or other arrangements.

FIG. 1C illustrates some ways in which some functionality of the device of FIG. 1A or 1B is provided not implanted in the subject. For example, in FIG. 1C an external power supply 140 is provided which can provide power to implanted elements of the device in ways familiar to the skilled person, and an external controller 150 provides part or all of the functionality of the controller 104, and/or provides other aspects of control of the device, and/or provides data readout from the device, and/or provides a data input facility 152. The data input facility could be used by a subject or other operator in various ways, for example to input data relating to the subject's current or expected activities such as sleep, eating, or physical exertion.

Each neuromodulation device may be adapted to carry out the neuromodulation required using one or more physical modes of operation which typically involve applying a signal to a carotid body or sinus nerve, such a signal typically involving a transfer of energy to (or from) the body or nerve. As already discussed, such modes may comprise modulating the carotid sinus nerve or body using an electrical signal, an optical signal, an ultrasound or other mechanical signal, a thermal signal, a magnetic or electromagnetic signal, or some other use of energy to carry out the required modulation. Such signals may be non-destructive signals. Such modulation may comprise increasing, inhibiting, or otherwise changing the pattern of neural activity in the nerve or body. To this end, the transducer 90 illustrated in FIG. 1A could be comprised of one or more electrodes, one or more photon sources, one or more ultrasound transducers, one more sources of heat, or one or more other types of transducer arranged to put the required neuromodulation into effect.

The neural modulation device(s) or apparatus may be arranged to inhibit neural activity of a carotid sinus nerve or carotid body by using the transducer(s) to apply an electrical signal, for example a voltage or current, for example a direct current (DC) such as a charge balanced direct current, or an AC waveform, or both. In such embodiments, the transducers configured to apply the electrical signal are electrodes.

In certain embodiments, the electrical signal applied by the one or more transducers has a frequency of 0.5 to 100 kHz, optionally 1 to 50 kHz, optionally 5 to 50 KHz. In certain embodiments the signal has a frequency of 25 to 55 kHz, optionally 30-50 kHz. In certain embodiments, the signal has a frequency of 5-10 KHz. In certain embodiments, the electrical signal has a frequency of greater than 20 kHz, optionally at least 25 kHz, optionally at least 30 kHz. In certain embodiments the signal has a frequency of 30 kHz, 40 kHz or 50 kHz.

In certain embodiments, an onset response as a result of the signal being applied can be avoided if the signal does not have a frequency of 20 kHz or lower, for example 1-20 kHz, or 1-10 kHz.

In certain embodiments the DC waveform or AC waveform may be a square, sinusoidal, triangular or complex waveform. The DC waveform may alternatively be a constant amplitude waveform. In certain embodiments the electrical signal is an AC sinusoidal waveform.

It will be appreciated by the skilled person that the current amplitude of an applied electrical signal necessary to achieve the intended neuromodulation will depend upon the positioning of the electrode and the associated electrophysiological characteristics (e.g. impedance). It is within the ability of the skilled person to determine the appropriate current amplitude for achieving the intended neuromodulation in a given subject. For example, the skilled person is aware of methods suitable to monitor the neural activity profile induced by neuromodulation.

In certain embodiments, the electrical signal has a current of 0.1-10 mA, optionally 0.5-5 mA, optionally 1 mA-2 mA, optionally 1 mA or 2 mA.

In certain embodiments, the signal is an electrical signal comprising an AC sinusoidal waveform having a frequency of greater than 25 kHz, optionally 30-50 kHz.

In those embodiments wherein one or more transducers are electrodes, the electrode may be a bipolar electrode, or a tripolar electrode. The electrode may be a cuff electrode or a wire electrode.

Thermal methods of neuromodulation typically manipulate the temperature of a nerve to inhibit signal propagation. For example, Patberg et al. (Blocking of impulse conduction in peripheral nerves by local cooling as a routine in animal experimentation. Journal of Neuroscience Methods 1984; 10:267-75, which is incorporated herein by reference) discuss how cooling a nerve blocks signal conduction without an onset response, the block being both reversible and fast acting, with onsets of up to tens of seconds. Heating the nerve can also be used to block conduction, and is generally easier to implement in a small implantable or localised transducer or device, for example using infrared radiation from laser diode or a thermal heat source such as an electrically resistive element, which can be used to provide a fast, reversible, and spatially very localised heating effect (see for example Duke et al. J Neural Eng. 2012 June; 9(3):036003. Spatial and temporal variability in response to hybrid electro-optical stimulation, which is incorporated herein by reference). Either heating, or cooling, or both could be provided using a Peltier element.

In certain embodiments wherein the signal applied by the one or more transducers is a thermal signal, the signal reduces the temperature of the nerve (i.e. cools the nerve). In certain such embodiments the nerve is cooled to 14° C. or lower to partially inhibit neural activity, or to 6° C. or lower, for example 2° C., to fully inhibit neural activity. In such embodiments, it is preferably not to cause damage to the nerve. In certain alternative embodiments, the signal increases the temperature of the nerve (i.e. heats the nerve). In certain embodiments, neural activity is inhibited by increasing the nerve by at least 5° C., for example by 5° C., 6° C., 7° C., 8° C. In certain embodiments, the signal both heats and cools the nerve, simultaneously at different locations on the nerve, or sequentially at the same or different location on the nerve.

In those embodiments in which the signal applied by the one or more transducers is a thermal signal, at least one of the one or more transducers is a transducer configured to apply a thermal signal. In certain such embodiments, all the transducers are configured to apply a thermal signal, optionally the same thermal signal.

In certain embodiments, one or more of the one or more transducers comprise a Peltier element configured to apply a thermal signal, optionally all of the one or more transducers comprise a Peltier element. In certain embodiments, one or more of the one or more transducers comprise a laser diode configured to apply a thermal signal, optionally all of the one or more transducers comprise a laser diode configured to apply a thermal signal. In certain embodiments, one or more of the one or more transducers comprise a electrically resistive element configured to apply a thermal signal, optionally all of the one or more transducers comprise a electrically resistive element configured to apply a thermal signal.

Optogenetics is a technique that genetically modifies cells to express photosensitive features, which can then be activated with light to modulate cell function. Many different optogenetic tools have been developed that can be used to inhibit neural firing. A list of optogenetic tools to suppress neural activity has been compiled (Epilepsia. 2014 Oct. 9. doi: 10.1111/epi.12804. WONOEP appraisal: Optogenetic tools to suppress seizures and explore the mechanisms of epileptogenesis. Ritter L M et al., which is incorporated herein by reference). Acrylamine-azobenzene-quaternary ammonium (AAQ) is a photochromic ligand that blocks many types of K+ channels and in the cis configuration, the relief of K+ channel block inhibits firing (Nat Neurosci. 2013 July; 16(7):816-23. doi: 10.1038/hn.3424. Optogenetic pharmacology for control of native neuronal signaling proteins. Kramer R H et al, which is incorporated herein by reference).

In certain embodiments the signal applied by the one or more transducers is an electromagnetic signal, optionally an optical signal. In certain such embodiments, the one or more transducers comprise a laser and/or a light emitting diode configured to apply the optical signal. In certain such embodiments, the optical signal (for example the laser signal) has an energy density from 500 mW/cm$^2$ to 900 W/cm$^2$. In certain alternative embodiments, the signal is a magnetic signal. In certain such embodiments, the magnetic signal is a biphasic signal with a frequency of 5-15 Hz, optionally 10 Hz. In certain such embodiments, the signal has a pulse duration of 1-1000 µS, for example 500 µS.

In certain embodiments the signal applied by the one or more transducers is an electromagnetic signal, optionally an optical signal. In certain such embodiments, the one or more transducers comprise a laser and/or a light emitting diode configured to apply the optical signal. In certain such embodiments, the optical signal (for example the laser signal) has an energy density from 500 mW/cm$^2$ to 900 W/cm$^2$. In certain alternative embodiments, the signal is a magnetic signal. In certain such embodiments, the magnetic signal is a biphasic signal with a frequency of 5-15 Hz, optionally 10 Hz. In certain such embodiments, the signal has a pulse duration of 1-1000 µS, for example 500 µS.

Mechanical forms of neuromodulation can include the use of ultrasound which may conveniently be implemented using external instead of implanted ultrasound transducers. Other forms of mechanical neuromodulation include the use of pressure (for example see "The effects of compression upon conduction in myelinated axons of the isolated frog sciatic nerve" by Robert Fern and P. J. Harrison Br.j. Anaesth. (1975), 47, 1123, which is incorporated herein by reference.

In certain embodiments the signal applied by the one or more transducers is a mechanical signal. In certain embodiments, the mechanical signal is a pressure signal. In certain such embodiments, the transducer causes a pressure of at least 250 mmHg to be applied to the nerve, thereby inhibiting neural activity. In certain alternative embodiments, the signal is an ultrasonic signal. In certain such embodiments, the ultrasonic signal has a frequency of 0.5-2.0 MHz, optionally 0.5-1.5 MHz, optionally 1.1 MHz. In certain embodiments, the ultrasonic signal has a density of 10-100 W/cm$^2$, for example 13.6 W/cm$^2$ or 93 W/cm$^2$.

Some other electrical forms of neuromodulation may use direct current (DC), or alternating current (AC) waveforms applied to a nerve using one or more electrodes. A DC block may be accomplished by gradually ramping up the DC waveform amplitude (Bhadra and Kilgore, IEEE Transactions on Neural systems and rehabilitation engineering, 2004 12(3) pp 313-324).

Some other AC techniques include HFAC or KHFAC (high-frequency or kilohertz frequency) to provide a reversible block (for example see Kilgore and Badra, 2004, Medical and Biological Engineering and Computing, May; 42(3):394-406. Nerve conduction block utilising high-frequency alternating current. Kilgore K L, Bhadra N.). In the work of Kilgore and Bhadra, a proposed waveform was sinusoidal or rectangular at 3-5 kHz, and typical signal amplitudes that produced block were 3-5 Volts or 0.5 to 2.0 milli Amperes peak to peak.

HFAC may typically be applied at a frequency of between 1 and 50 kHz at a duty cycle of 100% (Bhadra, N. et al., Journal of Computational Neuroscience, 2007, 22(3), pp 313-326). Methods for selectively blocking activity of a nerve by application of a waveform having a frequency of 5-10 kHz are described in U.S. Pat. No. 7,389,145. Similarly, U.S. Pat. No. 8,731,676 describes a method of ameliorating sensory nerve pain by applying a 5-50 kHz frequency waveform to a nerve.

Some commercially available nerve blocking systems include the Maestro® system available from Enteromedics Inc. of Minnesota, USA. Similar neuromodulation devices are more generally discussed in US2014/214129 and elsewhere.

In a further aspect, the invention provides a method of treating a condition associated with impaired glucose control in a subject, the method comprising applying a signal to a carotid sinus nerve (CSN) and/or a carotid body of said subject to modulate the neural activity of a CSN in the subject. In certain embodiments, this can be accomplished by the signal being applied by a neuromodulation device comprising one or more transducers for applying the signal. In certain preferred embodiments the neuromodulation device is at least partially implanted in the subject. In certain preferred embodiments, the neuromodulation device is wholly implanted in the subject.

As is known by the skilled person, each individual mammalian subject has a left and a right carotid body, each carotid body having an associated CSN. The CSN carries afferent nerve signals from the carotid body to the brain. Therefore, in methods according to the invention, the signal can be applied directly to a part of or all of one or both CSNs to modulate the neural activity in that or those CSNs. Alternatively, the signal can be applied to a part of or all of one or both carotid bodies associated with the CSNs in order to modulate the afferent nerve signals carried from the carotid body or bodies to the glossopharyngeal nerve and the brain stem. Alternatively, the signal can be applied to a part or all of both the carotid body and the associated CSN, unilaterally or bilaterally.

In certain embodiments of the method, the condition associated with impaired glucose control is a condition associated with insulin resistance. Examples of conditions associated with impaired glucose control include metabolic syndrome, type 2 diabetes, obesity, hypertension, dyslipidaemia, sleep apnoea syndrome and other metabolic disorders. In certain embodiments, the condition treated by the methods is at least one of the group consisting of metabolic syndrome, type 2 diabetes, obesity, and dyslipidaemia. The skilled person will appreciate that any one subject can exhibit one or more conditions associated with impaired glucose control and that the method can be used to treat one or more or all of those conditions.

In certain embodiments of the method, treatment of the condition is indicated by an improvement in a measurable physiological parameter, for example reduction in sympathetic tone, increase in insulin sensitivity, increase in glucose tolerance, a reduction in total fat mass, a reduction in visceral fat mass, a reduction in subcutaneous fat mass, reduction in plasma catecholamines, reduction in tissue catecholamines, reduction in urinary metanephrines, a reduction in glycated haemoglobin (HbA1c) or a reduction in circulating triglyceride concentration. In certain such embodiments, the measurable physiological parameter is at least one of the group consisting of: sympathetic tone, insulin sensitivity, glucose sensitivity, total fat mass, visceral fat mass, subcutaneous fat mass plasma catecholamines content, tissue catecholamines content urinary metanephrines content, and levels of glycated haemoglobin (HbA1c). In such embodiments, sympathetic tone is understood to be the neural activity in sympathetic nerves and/or associated sympathetic neurotransmitter measured in systemic or local tissue compartments in the sympathetic nervous system.

Suitable methods for determining the value for any given parameter would be appreciated by the skilled person. By way of example, an increase in heart rate and/or blood pressure for a period at least 24 hrs is typically indicative of an increased sympathetic tone, as is aberrant heart rate variability, cardiac or renal norepinephrine spillover, skin or muscle microneurography and plasma/urine norepinephrine By way of further example, insulin sensitivity can be measured by the HOMA index or by a hyperinsulinemic clamp. By way of further example, total fat mass may be determined by bioimpedance. By way of further example, visceral fat can be indirectly determined by measuring abdominal perimeter. Further suitable methods for determining the value for any given parameter would be appreciated by the skilled person.

In certain embodiments of the method, treatment of the condition is indicated by an improvement in the profile of neural activity in the CSN. That is, treatment of the condition is indicated by the neural activity in the CSN approaching the neural activity in a healthy individual.

In certain embodiments, the physiological response may be temporary. That is, upon cessation of the signal, the measured physiological parameter in which an improvement was induced by the signal returns substantially towards baseline neural activity within 1-60 seconds, or within 1-60 minutes, or within 1-24 hours, optionally 1-12 hours, optionally 1-6 hours, optionally 1-4 hours, optionally 1-2 hours, or within 1-7 days, optionally 1-4 days, optionally 1-2 days. In some instances, the physiological parameter returns substantially fully to baseline neural activity. That is, the value of the physiological parameter following cessation of the signal is substantially the same as the value for the physiological parameter prior to the signal being applied—i.e. prior to modulation.

In certain embodiments, the physiological response may be persistent. That is, upon cessation of the signal, the value of the measurable physiological parameter remains substantially the same as when the signal was being applied—i.e. the value for the physiological parameter during and following modulation is substantially the same In certain embodiments, the physiological response may be corrective. That is, upon cessation of the signal, the value of the measurable physiological parameter more closely resembles the value for that parameter observed in a healthy subject than prior to modulation, preferably substantially fully resembles the value for that parameter observed in a healthy subject.

In certain embodiments of the method, the method does not affect the cardiopulmonary regulation function of the carotid body and CSN. In particular embodiments, the method does not affect one or more physiological parameters in the subject selected from the group consisting of: pO2, pCO2, blood pressure, oxygen demand and cardiorespiratory responses to exercise and altitude. Suitable methods for determining the value for any given parameter would be appreciated by the skilled person.

According to the method of the invention, application of the signal results in the neural activity in at least part of the CSN being reduced compared to the baseline neural activity in that part of the nerve. Such a reduction in activity could equally be across the whole nerve, in which case neural activity would be reduced across the whole nerve. Therefore, in certain such embodiments, a result of applying the signal is at least partial inhibition of neural activity in the CSN. In certain such embodiments a result of applying the signal is at least partial inhibition of neural activity in the chemoreceptor branch of the CSN. In certain such embodiments, a result of applying the signal is full inhibition of neural activity in the chemoreceptor branch of the CSN. In certain embodiments, a result of applying the signal is full inhibition of neural activity in the CSN. Analogously, in certain embodiments the modulation in neural activity as a result of applying the signal is inhibition of neural activity from the carotid sinus/carotid body to the glossopharyngeal nerve and the brain stem, such that neural activity which is associated with the CSN/CB in the CSN, the glossopharyngeal nerve or the brain stem is reduced compared to pre-treatment neural activity associated with the carotid sinus/carotid body in that part of the nerve.

In certain embodiments of the method, the modulation in neural activity as a result of applying the signal is a block on neural activity in the CSN. That is, in such embodiments, the application of the signal blocks action potentials from travelling beyond the point of the block in at least a part of the CSN. In certain such embodiments, the modulation is a partial block. In certain alternative embodiments, the modulation is a full block.

In certain embodiments of the method, the modulation in neural activity as a result of applying the signal is an alteration to the pattern of action potentials in the CSN. In certain such embodiments, the neural activity is modulated such that the resultant pattern of action potentials in the CSN resembles the pattern of action potentials in the CSN observed in a healthy subject.

In certain embodiments of the method, the signal is applied intermittently. In certain such embodiments, the signal is applied continuously for at least 5 days, optionally at least 7 days, before ceasing. That is, for such intermittent application of the signal, the signal is applied continuously for at least 5 days (optionally 7 days), then application ceases for a period (e.g. 1 day, 2 days, 3 days, 1 week, 2 weeks, 1 month) before the signal is again applied continuously for at least 5 days (optionally 7 days).

In certain such embodiments wherein the signal is applied intermittently, the signal is applied for a first time period, then stopped for a second time period, then reapplied for a third time period, then stopped for a fourth time period. In such an embodiment, the first, second, third and fourth periods run sequentially and consecutively. The series of first, second, third and fourth periods amounts to one application cycle. In certain such embodiments, multiple application cycles can run consecutively such that the signal is applied in phases, between which phases no signal is applied.

In such embodiments, the duration of the first, second, third and fourth time periods is independently selected. That is, the duration of each time period may be the same or different to any of the other time periods. In certain such embodiments, the duration of each of the first, second, third and fourth time periods may be any time from 1 second (s) to 10 days (d), 2 s to 7 d, 3 s to 4 d, 5 s to 24 hours (24 h), 30 s to 12 h, 1 min to 12 h, 5 min to 8 h, 5 min to 6 h, 10 min to 6 h, 10 min to 4 h, 30 min to 4 h, 1 h to 4 h. In certain embodiments, the duration of each of the first, second, third and fourth time periods is 5, 10 s, 30 s, 60 s, 2 min, 5 min, 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 2 d, 3 d, 4 d, 5 d, 6 d, 7 d.

In certain embodiments wherein the signal is applied intermittently, the signal is applied for a specific amount of time per day. In certain such embodiments, the signal is applied for 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain such embodiments, the signal is applied continuously for the specified amount of time. In certain alternative such embodiments, the signal may be applied discontinuously across the day, provided the total time of application amounts to the specified time.

In certain embodiments wherein the signal is applied intermittently, the signal is applied only when the subject is in a specific state. In certain such embodiments, the signal is applied only when the subject is awake. In certain alternative embodiments, the signal is applied only when the subject is asleep. In certain embodiments, the signal is applied prior to and/or after the ingestion of food. In certain embodiments, the signal is applied prior to and/or after the subject undertakes exercise. In such embodiments, the status of the subject (i.e. whether the subject is awake, asleep, pre- or post-eating, or pre- or post-taking exercise) can be indicated by the subject. In alternative such embodiments, the status of the subject can be detected independently from any input from the subject. In certain embodiments in which the signal is applied by a neuromodulation device, the device further comprises a detector configured to detect the status of the subject, wherein the signal is applied only when the detector detects that the subject is in the specific state.

In certain alternative embodiments, the controller causes the signal to be continuously applied to the CSN and/or carotid body. It will be appreciated that in embodiments wherein the signal is a series of pulses, gaps between pulses do not mean the signal is not continuously applied. Such continuous application may continue indefinitely, e.g. permanently. Alternatively, the continuous application may be for a minimum period, for example the signal may be continuously applied for at least 5 days, or at least 7 days.

In certain embodiments of the method, the modulation in neural activity caused by the application of the signal (whether that is an inhibition, block or other modulation of neural activity) is temporary/reversible. That is, upon cessation of the signal, neural activity in the nerve returns substantially towards baseline neural activity within 1-60 seconds, or within 1-60 minutes, or within 1-7 days, optionally 1-4 days, optionally 1-2 days, or within 1-24 hours, optionally 1-12 hours, optionally 1-6 hours, optionally 1-4 hours, optionally 1-2 hours. In certain such embodiments, the neural activity returns substantially fully to baseline neural activity. That is, the neural activity following cessation of the signal is substantially the same as the neural activity prior to the signal being applied—i.e. prior to modulation.

In certain alternative embodiments of the method, the modulation in neural activity caused by the application of the signal is substantially persistent. That is, upon cessation of the signal, neural activity in the nerve remains substantially the same as when the signal was being applied—i.e. the neural activity during and following modulation is substantially the same.

In certain embodiments of the method, the modulation in neural activity caused by the application of the signal is partially corrective, preferably substantially corrective. That is, upon cessation of the signal, neural activity in the nerve more closely resembles the pattern of action potentials in the CSN observed in a healthy subject than prior to modulation, preferably substantially fully resembles the pattern of action potentials in the CSN observed in a healthy subject. In such embodiments, the modulation caused by the signal can be any modulation as defined herein. For example, application of the signal may result in a block on neural activity, and upon cessation of the signal, the pattern of action potentials in the nerve resembles the pattern of action potentials observed in a healthy subject. By way of further example, application of the signal may result modulation such that the neural activity resembles the pattern of action potentials observed in a healthy subject, and upon cessation of the signal, the pattern of action potentials in the nerve resembles the pattern of action potentials observed in a healthy subject. It is hypothesised that such a corrective effect is the result of a positive feedback loop—that is, the underlying disease state is treated as result of the claimed methods, and therefore the chemosensory signals along the CSN are not abnormal, and therefore the disease state is not perpetuated by the abnormal CSN neural activity.

In certain embodiments of method according to the invention, the method further comprises the step of detecting one or more physiological parameters of the subject, wherein the signal is applied only when the detected physiological parameter meets or exceeds a predefined threshold value. In such embodiments wherein more than one physiological parameter is detected, the signal may be applied when any one of the detected parameters meets or exceeds its threshold value, alternatively only when all of the detected parameters meet or exceed their threshold values. In certain embodiments wherein the signal is applied by a neuromodulation device, the device further comprises at least one detector configured to detect the one or more physiological parameters.

In certain embodiments of the method, the one or more detected physiological parameters are one or more of the group consisting of: sympathetic tone, plasma insulin concentration, insulin sensitivity, plasma glucose concentration, glucose tolerance, total far mass, visceral fat mass, plasma catecholamines (i.e. one or more of epinephrine, norepinephrine, metanephrine, normetanephrine and dopamine) content, tissue catecholamines content urinary metanephrines content, plasma HbA1c content and a reduction in circulating triglyceride concentration.

By way of example, a typical HbA1c content in a healthy human subject would be between 20-42 mmol/mol (4-6% of total Hb). An HbA1c content exceeding 42 mmol/mol may be indicative of a diabetic state.

In certain embodiments, the one or more detected physiological parameters are one or more of the group consisting of: sympathetic tone, plasma insulin concentration, plasma glucose concentration, plasma catecholamines (i.e. one or more of epinephrine, norepinephrine, metanephrine, normetanephrine) concentration, tissue catecholamines, and plasma HbA1c content.

In certain embodiments, the detected physiological parameter is an action potential or pattern of action potentials in a nerve of the subject, wherein the action potential or pattern of action potentials is associated with the condition associated with an impaired response to glucose that is to be treated. In certain such embodiments, the nerve is a sympathetic nerve.

In certain such embodiments, the nerve is an afferent sympathetic nerve. In certain such embodiments, the nerve is the CSN. In this embodiment, the detected pattern of action potentials may be associated with impaired response to glucose. In certain alternative such embodiments, the nerve is an afferent nerve involved in metabolic regulation, for example afferent nerves from the liver or from the GI tract.

In certain alternative such embodiments, the nerve is an efferent sympathetic nerve, optionally the peroneal nerve, the sciatic nerve (or one or more branches thereof), or muscle sympathetic nerve terminals. In certain such embodiments, the nerve is the sciatic nerve. In certain such embodiments, the nerve is the renal nerve.

It will be appreciated that any two or more of the indicated physiological parameters may be detected in parallel or consecutively. For example, in certain embodiments, the pattern of action potentials in the CSN can be detected at the same time as glucose tolerance.

In certain such embodiments, once first applied, the signal may be applied intermittently or permanently, as described in the embodiments above.

Figure 9:
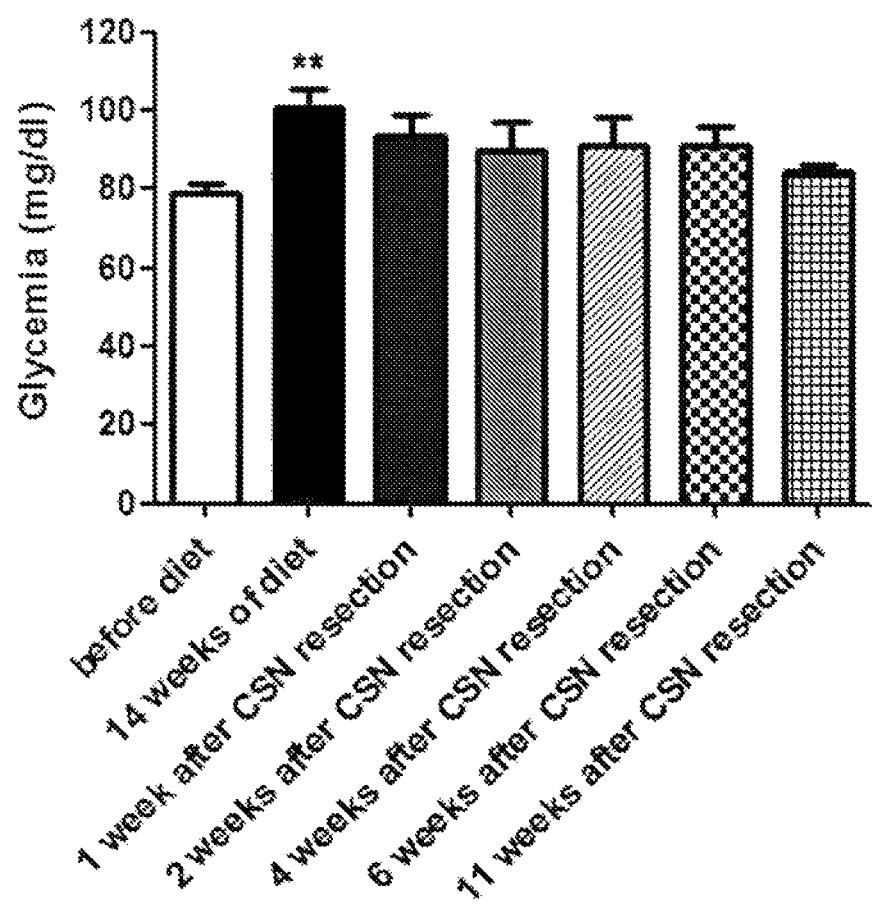
FIG. 9: Effect of chronic carotid sinus nerve (CSN) bilateral denervation on fasting plasma glucose in hypercaloric (High-fat (HF)±High sucrose (HSu)) animals. CSN resection was performed after 14 weeks of HF+HSu diet. One-way ANOVA with Dunnett's multiple comparison test. **p<0.01 vs values in animals before initiating HF+HSu diet. Data represent means±SEM.
Figure 10:
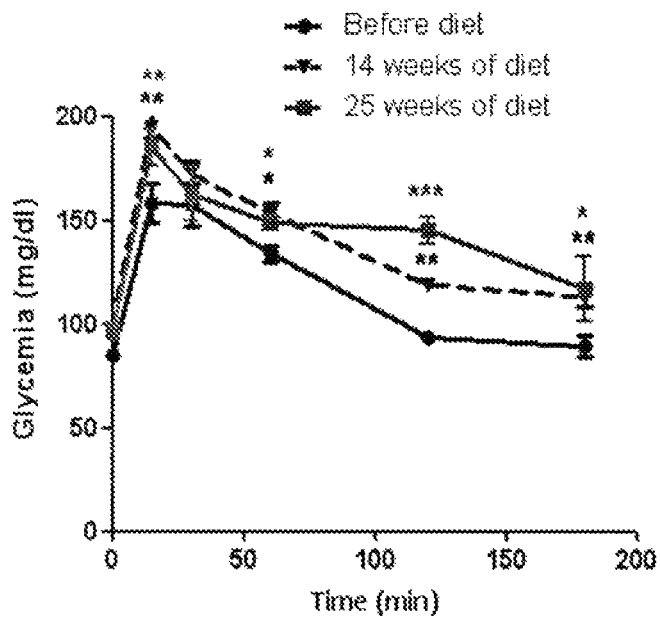
FIG. 10: A: Oral glucose tolerance in an animal model of type II diabetes (Wistar rats submitted to 14 and 25 weeks of HF+Hsu diet). B: Effect of bilateral carotid sinus nerve denervation at 14 weeks on glucose tolerance in animal model of type II diabetes (Wistar rats submitted to 14 and 25 weeks of HF+Hsu diet, with bilateral CSN denervation at 14 weeks (14 week readings taken prior to denervation)).
Figure 10:
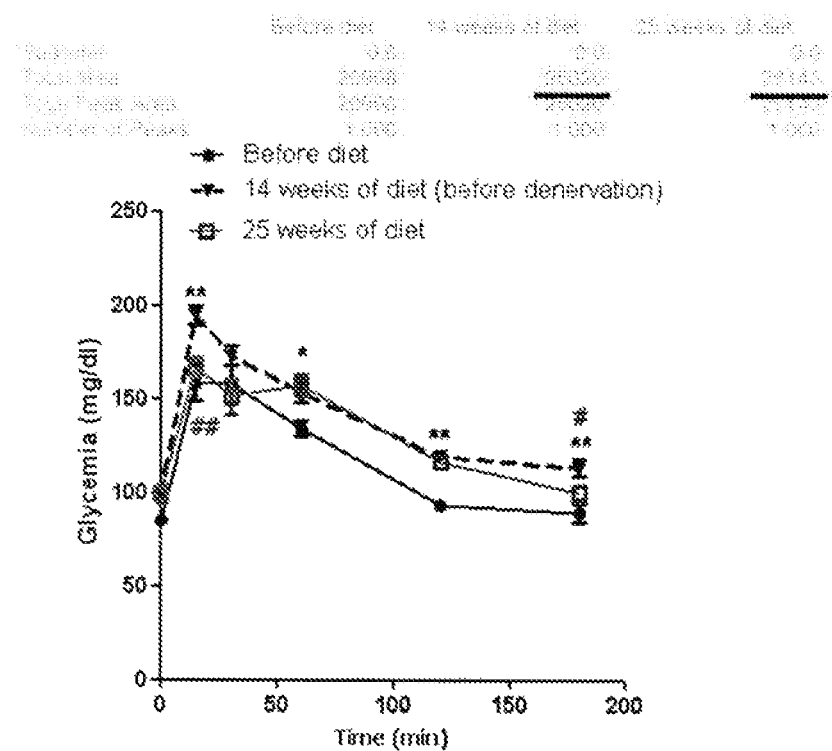
Figure 20:
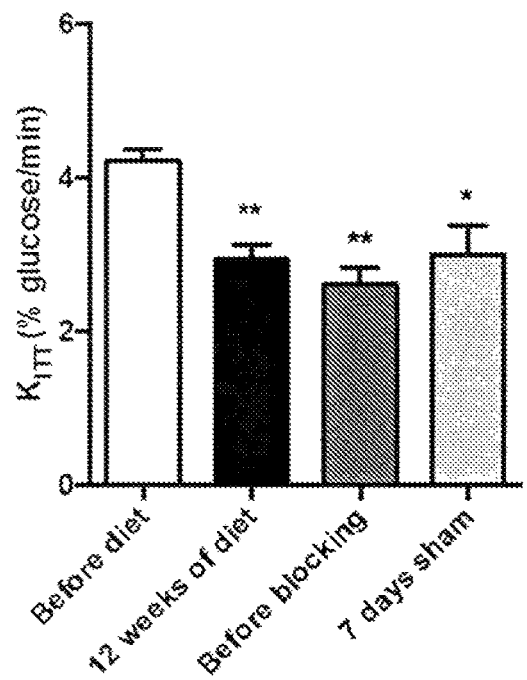
FIG. 20: $K_{ITT}$ of animals from sham (A) and active intervention (B) groups. *p<0.05. **p<0.01, for comparison with before diet baseline; #p<0.05, for comparison between 13 weeks of diet and 7 days after blocking
Figure 20:
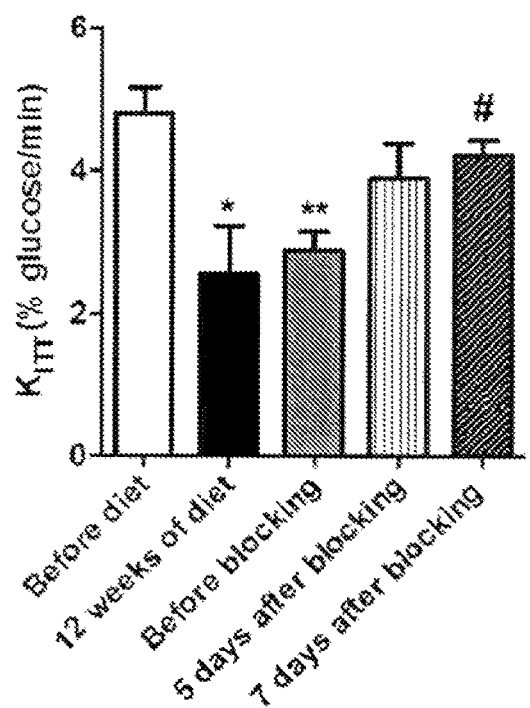
Figure 21:
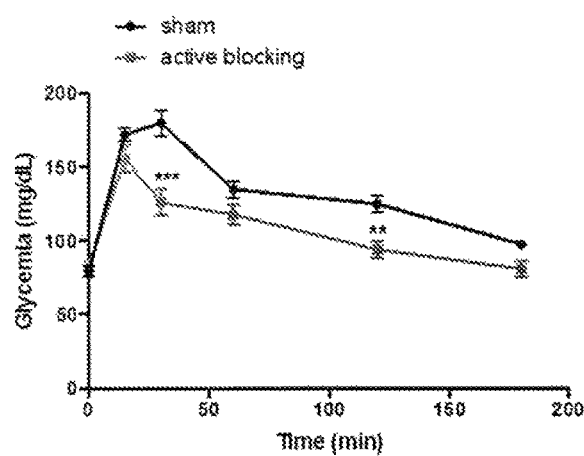
FIG. 21: OGTT of animals in sham and active intervention groups. A shows OGTT between the sham group and the intervention group. B (block) and C (sham) show OGTT for each group at each stage of the procedure. *p<0.05, p<0.01, *p<0.001 for comparison with before diet baseline; ##p<0.01, ###p<0.001 for comparison between 13 weeks of diet and 7 days after blocking
Figure 21:
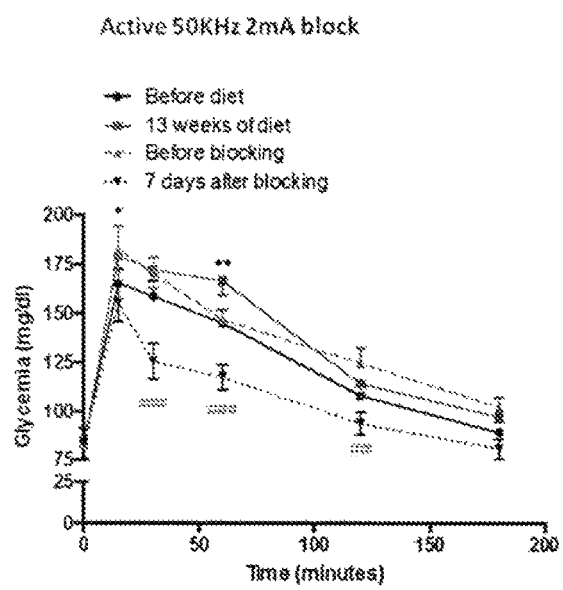
Figure 21:
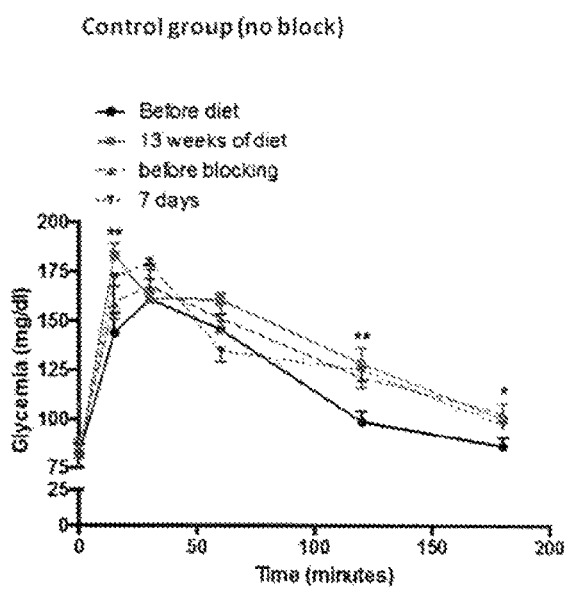

As demonstrated herein, stopping or inhibiting neural signalling in one CSN (i.e. unilateral modulation) is sufficient to at least partially restore insulin sensitivity (FIG. 10), although this effect may be transient. Therefore in certain embodiments, a signal is applied to a carotid sinus nerve (CSN) and/or a carotid body of said subject to modulate the neural activity of a CSN in the subject. That is, the signal is applied at least unilaterally to achieve at least unilateral (i.e. right or left side) modulation of neural activity in the respective CSN. In FIG. 9, it is clear that stopping neural signalling in both CSNs (i.e. bilateral modulation) produces a greater effect that is longer-lasting. Similarly, FIGS. 20 and 21 show that bilateral block of CSN neural activity using an electrical signal is effective at restoring glucose tolerance and insulin sensitivity. A greater improvement is observed the longer the block is applied (FIG. 20).

Therefore, in certain preferred embodiments of the method, the neural activity in both CSNs is modulated (i.e. the modulation is bilateral). That is, in certain preferred embodiments, a signal is applied to the left carotid sinus nerve (CSN) and/or left carotid body of the subject and a signal is applied to the right carotid sinus nerve (CSN) and/or right carotid body of the subject to modulate the neural activity of the left CSN and right CSN of the subject. In such embodiments, the signal applied to each CSN and/or carotid body, and therefore the type and extent of modulation, is independently selected from that applied to the opposite CSN and/or carotid body. In certain embodiments the signal applied to the right CSN and/or carotid body is the same as the signal applied to the left CSN and/or carotid body. In certain alternative embodiments the signal applied to the right CSN and/or carotid body is different to the signal applied to the left CSN and/or carotid body.

In certain such embodiments of the method, a first signal is applied to the left carotid sinus nerve (CSN) and/or left carotid body of the subject to modulate the neural activity of the left CSN in the subject by a neuromodulation device comprising one or more transducers for applying the signal, and a second signal is applied to the right carotid sinus nerve (CSN) and/or right carotid body of said subject to modulate the neural activity of the right CSN in the subject by a neuromodulation device comprising one or more transducers for applying the signal. In certain such embodiments, the first signal and the second signal are applied by the same neuromodulation device, that device have at least two transducers, one to apply the first signal and one to apply the second signal. In certain alternative such embodiments, the first and second signals are applied by separate neuromodulation devices.

It should be noted that the temporary nature of the therapeutic effect when CSN activity is stopped unilaterally (FIG. 10) may be due to the total and ongoing block of one CSN (i.e. by resection) being compensated for by the remaining CSN. It may be that intermittent or temporary unilateral modulation would not exhibit the reduced effect, as the remaining CSN would not be caused to compensate.

In certain embodiments of the method, the signal applied is a non-destructive signal.

In certain embodiments of the method according to the invention, the signal applied is an electrical signal, an electromagnetic signal (optionally an optical signal), a mechanical (optionally ultrasonic) signal, a thermal signal, a magnetic signal or any other type of signal. In certain such embodiments in which more than one signal may be applied, for example one to each CSN and/or carotid body, each signal may be independently selected from an electrical signal, an optical signal, an ultrasonic signal, and a thermal signal. In those such embodiments in which two signals are applied by one modulation device, the two signals may be the same type of signal or may be different types of signal independently selected from an electrical signal, an optical signal, an ultrasonic signal, and a thermal signal. In those embodiments in which two signals are applied, each by a separate neuromodulation device, the two signals may be the same type of signal or may be different types of signal independently selected from an electrical signal, an optical signal, an ultrasonic signal, and a thermal signal.

In certain embodiments of the method in which the signal is applied by a neuromodulation device comprising at least one transducer, the transducer may be comprised of one or more electrodes, one or more photon sources, one or more ultrasound transducers, one more sources of heat, or one or more other types of transducer arranged to put the signal into effect.

In certain embodiments of the method the signal is an electrical signal, for example a voltage or a current, and comprises one or more AC or DC waveforms. In certain embodiments, the electrical signal is an AC waveform having a frequency of 0.5 to 100 kHz, optionally 1 to 50 kHz, optionally 5 to 50 KHz. In certain embodiments the signal has a frequency of 25 to 55 kHz, optionally 30-50 kHz. In certain embodiments, the signal has a frequency of 5-10 KHz. In certain embodiments, the electrical signal has a frequency of greater than 1 kHz.

It is shown herein that electrical signals having a frequency of more than 20 kHz are particularly effective at inhibiting (in particular, blocking) neural activity of the CSN. Therefore, in certain preferred embodiments of the method the electrical signal has a frequency greater than 20 kHz, optionally at least 25 kHz, optionally at least 30 kHz. In certain embodiments the signal has a frequency of 30 kHz, 40 kHz or 50 kHz.

In certain embodiments, an onset response as a result of the signal being applied can be avoided if the signal does not have a frequency of 20 kHz or lower, for example 1-20 kHz, or 1-10 KHz.

In certain embodiments the DC waveform or AC waveform may be a square, sinusoidal, triangular or complex waveform. The DC waveform may alternatively be a constant amplitude waveform. In certain embodiments the electrical signal is an AC sinusoidal waveform.

It will be appreciated by the skilled person that the current amplitude of an applied electrical signal necessary to achieve the intended neuromodulation will depend upon the positioning of the electrode and the associated electrophysiological characteristics (e.g. impedance). It is within the ability of the skilled person to determine the appropriate current amplitude for achieving the intended neuromodulation in a given subject. For example, the skilled person is aware of methods suitable to monitor the neural activity profile induced by neuromodulation.

In certain embodiments, the electrical signal has a current of 0.5-5 mA, optionally 0.5 mA-2 mA, optionally 0.5-1.5 mA, optionally 1 mA or 2 mA.

In certain embodiments, the signal is an electrical signal comprising an AC sinusoidal waveform having a frequency of greater than 25 kHz, optionally 30-50 kHz. In certain such embodiments, the signal is an electrical signal comprising an AC sinusoidal waveform having a frequency of greater than 25 kHz, optionally 30-50 kHz having a current of 1 mA or 2 mA.

In those embodiments in which the electrical signal is applied by a neuromodulation device comprising one or more electrodes, each transducer configured to apply the signal is an electrode configured to apply the electrical signal. In certain such embodiments, all the transducers are electrodes configured to apply an electrical signal, optionally the same electrical signal. In certain such embodiments, the electrode may be a bipolar electrode, or a tripolar electrode. The electrode may be a cuff electrode or a wire electrode.

In certain embodiments wherein the signal applied by the one or more transducers is a thermal signal, the signal reduces the temperature of the nerve (i.e. cools the nerve). In certain such embodiments the nerve is cooled to 14° C. or lower to partially inhibit neural activity, or to 4° C. or lower, for example 2° C., to fully inhibit neural activity. In such embodiments, it is preferably not to cause damage to the nerve. In certain alternative embodiments, the signal increases the temperature of the nerve (i.e. heats the nerve). In certain embodiments, neural activity is inhibited by increasing the nerve by at least 5° C., for example by 5° C., 6° C., 7° C., 8° C. In certain embodiments, the signal both heats and cools the nerve, simultaneously at different locations on the nerve, or sequentially at the same or different location on the nerve.

In those embodiments in which the signal applied by the one or more transducers is a thermal signal, at least one of the one or more transducers is a transducer configured to apply a thermal signal. In certain such embodiments, all the transducers are configured to apply a thermal signal, optionally the same thermal signal.

In certain embodiments, one or more of the one or more transducers comprise a Peltier element configured to apply a thermal signal, optionally all of the one or more transducers comprise a Peltier element. In certain embodiments, one or more of the one or more transducers comprise a laser diode configured to apply a thermal signal, optionally all of the one or more transducers comprise a laser diode configured to apply a thermal signal. In certain embodiments, one or more of the one or more transducers comprise a electrically resistive element configured to apply a thermal signal, optionally all of the one or more transducers comprise a electrically resistive element configured to apply a thermal signal.

In certain embodiments the signal applied by the one or more transducers is a mechanical signal. In certain embodiments, the mechanical signal is a pressure signal. In certain such embodiments, the transducer causes a pressure of at least 250 mmHg to be applied to the nerve, thereby inhibiting neural activity. In certain alternative embodiments, the signal is an ultrasonic signal. In certain such embodiments, the ultrasonic signal has a frequency of 0.5-2.0 MHz, optionally 0.5-1.5 MHz, optionally 1.1 MHz. In certain embodiments, the ultrasonic signal has a density of 10-100 $W/cm^2$, for example 13.6 $W/cm^2$ or 93 $W/cm^2$.

In certain embodiments the signal applied by the one or more transducers is an electromagnetic signal, optionally an optical signal. In certain such embodiments, the one or more transducers comprise a laser and/or a light emitting diode configured to apply the optical signal. In certain such embodiments, the optical signal (for example the laser signal) has an energy density from 500 $mW/cm^2$ to 900 $W/cm^2$. In certain alternative embodiments, the signal is a magnetic signal. In certain such embodiments, the magnetic signal is a biphasic signal with a frequency of 5-15 Hz, optionally 10 Hz. In certain such embodiments, the signal has a pulse duration of 1-100 µS, for example 500 µS.

In a further aspect, the invention provides a neuromodulatory electrical waveform for use in treating insulin resistance in a subject, wherein the waveform is a kiloHertz alternating current (AC) waveform having a frequency of 1 to 50 KHz, optionally 25-50 kHz, such that, when applied to a carotid sinus nerve (CSN) of the subject, the waveform inhibits neural signalling in the CSN. In certain embodiments, the waveform, when applied to the CSN, improves the subject's response to insulin.

In a further aspect, the invention provides use of a neuromodulation device for treating a condition associated with impaired glucose control in a subject such as insulin resistance, by modulating afferent neural activity in a carotid sinus nerve of the subject.

Based on the observations presented herein, in particular the observation that CSN denervation results in lowering of the circulating plasma triglyceride concentration, it will be appreciated that in a still further aspect, the invention provides a method of treating obesity in a subject, the method comprising applying a signal to a carotid sinus nerve (CSN) and/or a carotid body of said subject to modulate the neural activity of a CSN in the subject. Further still, in another aspect, the invention provides a method of treating obesity, the method comprising applying a signal to a carotid sinus nerve (CSN) and/or a carotid body of said subject to modulate the neural activity of a CSN in the subject, wherein the signal is applied by a neuromodulation device comprising one or more transducers for applying the signal. The embodiments presented above with respect to the third and fourth aspects of the invention will be applicable, mutatis mutandis, to these aspects of the invention.

In a preferred embodiment of all aspects of the invention, the subject or patient is a mammal, more preferably a human. In certain embodiments, the subject or patient is suffering from a disease or disorder associated with impaired glucose control.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

EXAMPLES

Example 1

Animals and Experimental Procedures

Figure 2:
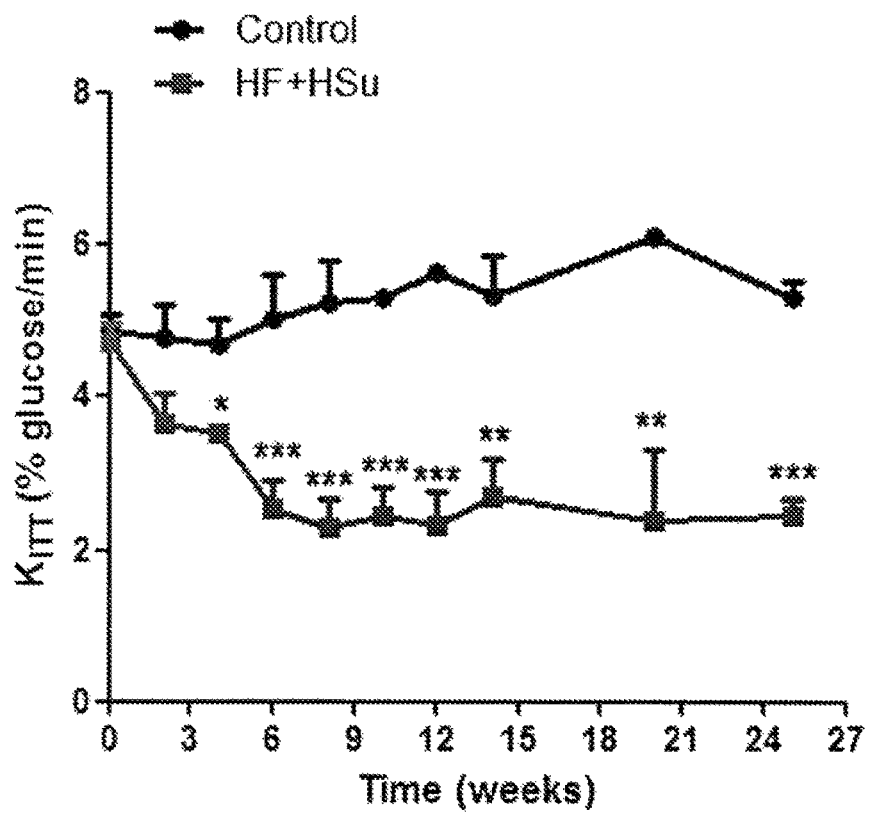
FIG. 2: Effect of hypercaloric diet ingestion (High-fat (HF)+High sucrose (HSu)) during 25 weeks diet on insulin sensitivity as used in the type II diabetic rat model, determined by the insulin tolerance test, expressed as the constant rate for glucose disappearance ($K_{ITT}$). One-way ANOVA with Dunnett's multiple comparison test. *p<0.05, p<0.01, *p<0.001 vs values in animals at 0 weeks of diet. Data represent means±SEM.
Figure 4:
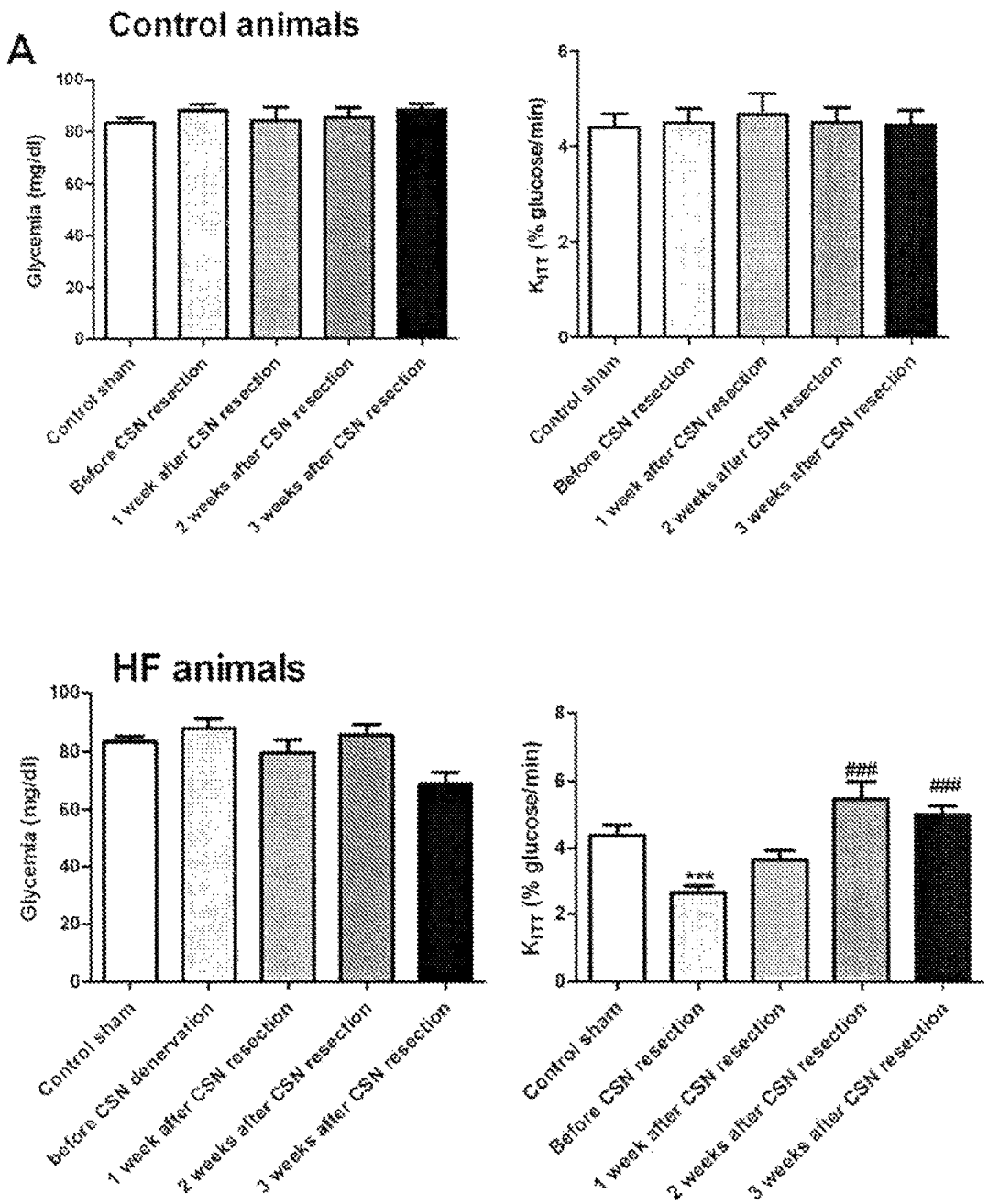
FIG. 4: Effect of carotid sinus nerve (CSN) denervation on fasting plasma glucose (left panels) and insulin sensitivity (right panels) determined by the insulin tolerance test, expressed as the constant rate for glucose disappearance ($K_{ITT}$) in control rats (A) and high-fat (HF) diet (prediabetic) rats (B). White bars represent values of fasting plasma glucose and insulin sensitivity in control animals without (CSN) denervation. Colour bars represent values of plasma glucose and insulin sensitivity in rats before and after CSN denervation. Rats were submitted to 3 weeks of HF diet, denervated at the $3^{rd}$ week and maintained during more 3 weeks under the respective diets.
Figure 5:
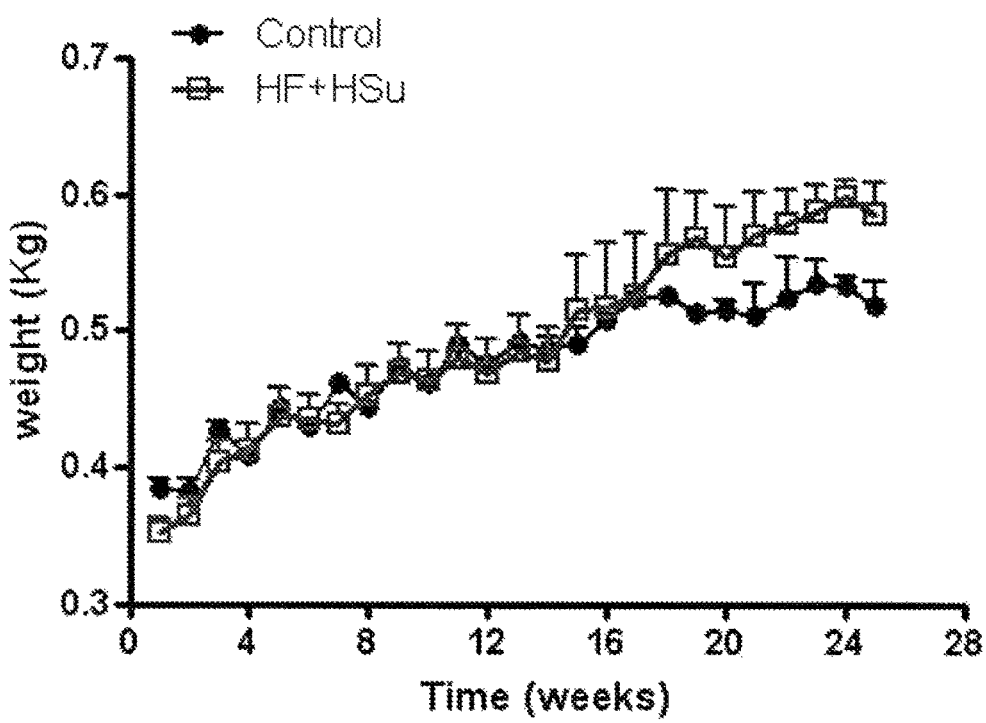
FIG. 5: Effect of hypercaloric diet ingestion (High-fat (HF)+High sucrose (HSu)) during 25 weeks diet on weight gain, as used in the type II diabetic rat model. Data represent means±SEM.
Figure 8:
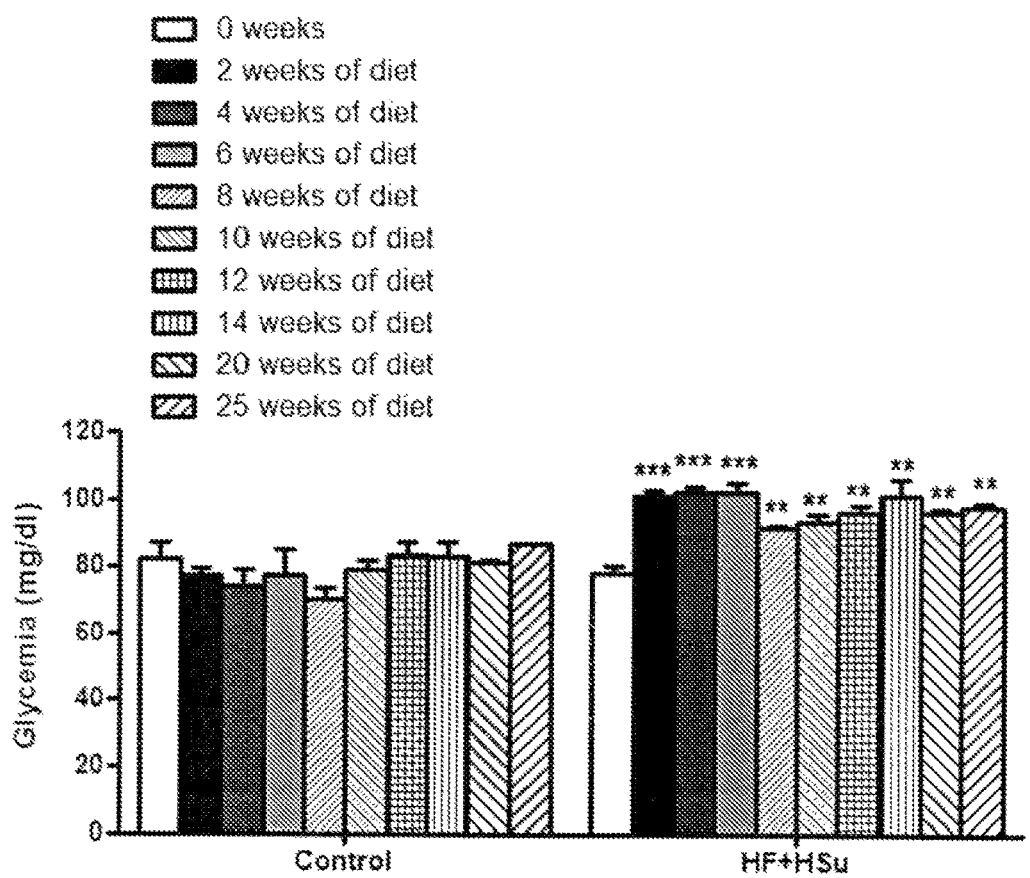
FIG. 8: Effect of hypercaloric diet ingestion (High-fat (HF)±High sucrose (HSu)) during 25 weeks on fasting plasma glucose. One-way ANOVA with Dunnett multiple comparison test. p<0.01, *p<0.001 comparing values with animals at 0 weeks of diet. Data are presented as means±SEM.

Experiments were performed in male Wistar rats (200-380 g), aged 8-9 weeks, obtained from the animal house of the NOVA Medical School, NOVA University of Lisbon. The animals were kept under temperature and humidity control (21±1° C.; 55±10% humidity) with a 12 h light-12 h dark cycle. On the day before the experimental procedures, rats were fasted overnight and allowed free access to water. Three different groups of animals were used throughout the experiments: a control group, a prediabetes group and a type 2 diabetes group. The control group was fed a sham diet (7.4% fat plus 75% carbohydrate [4% sugar] plus 17% protein; SDS diets RM1; Probiológica, Lisbon, Portugal). The prediabetes group fed a 60% lipid rich diet during at least 3 weeks (60% fat plus 17% carbohydrate plus 23% protein; Mucedola, Milan, Italy)—a high fat (HF) diet. This prediabetes model resembles prediabetes in humans as it is characterized by hyperinsulinemia, insulin resistance, and normoglycemia (FIG. 4). The type 2 diabetes model was fed with a 60% lipid rich diet (60% fat plus 17% carbohydrate plus 23% protein; Mucedola, Milan, Italy) plus 35% of sucrose in drinking water at least 14 weeks—a high fat and high sugar (HF+Hsu) diet. This model resembles an initial phase of type 2 diabetes in humans and it is characterized by combined hyperglycemia, insulin resistance, glucose intolerance and hyperinsulinemia (la Fleur et al., 2011) (FIGS. 2, 5 and 8).

Wistar rats were submitted to HF diet for at least 3 weeks to induce prediabetes and to HF+Hsu diets for at least 14 weeks in order to induce type 2 diabetes and were then submitted to bilateral carotid sinus nerve resection under ketamine (30 m/kg)/xylazine (4 mg/kg) anesthesia and brupenorphine (10 µg/kg) analgesia as described in Ribeiro et al., 2013, which is incorporated herein by reference. The control groups were submitted to a sham procedure. Food and liquid intake were monitored during the treatments in all groups of animals.

After the surgical procedure the animals were kept under the respective diets to maintain an increased caloric ingestion during the recovery period and the remaining experimental period (3 weeks for the prediabetes model and 11 weeks for the type 2 diabetes model). Pasting glucose (FIGS. 8 and 9 for type 2 diabetic rats, FIG. 4 for prediabetic rats), glucose tolerance (FIG. 10 for type 2 diabetic rats) and insulin sensitivity (FIGS. 2 and 3 for type 2 diabetic rats and FIG. 4 for diabetic rats) were evaluated before and after the carotid sinus nerve denervation. CSN resection was confirmed through the absence of ischemic hypoxia-induced hyperventilation assessed as occlusion of common carotid artery (Ribeiro et al., 2013). Principles of laboratory care were followed in accordance with the European Union Directive for Protection of Vertebrates Used for Experimental and other Scientific Ends (2010/63/U). Experimental protocols were approved by the ethics committee of the NOVA Medical School, NOVA University of Lisbon.

Measurement of Insulin Sensitivity

Insulin sensitivity was determined by the insulin tolerance test (ITT). The ITT provides an estimate of overall insulin sensitivity, correlating well with the 'gold standard' hyperinsulinemic-euglycemic clamp (Honzillo and Hamdy 2003, which is incorporated herein by reference). It involves the administration of an intravenous insulin bolus of 0.1 u/kg body weight in the tail vein, after an overnight fast, followed by the measurement of the decline in plasma glucose concentration over 15 minutes. The constant rate for glucose disappearance ($K_{ITT}$) was calculated using the formula $0.693/t_{1/2}$ (Monzillo and Hamdy 2003; Guarino et al., 2013; Ribeiro et al., 2013, all of which are incorporated herein by reference). Glucose halt-time ($t_{1/2}$) was calculated from the slope of the least square analysis of plasma glucose concentrations during the linear decay phase. Blood samples were collected by tail tipping and glucose levels were measured with a glucometer (Precision Xtra Meter, Abbott Diabetes Care, Portugal) and test strips (Abbott Diabetes Care, Portugal).

Figure 3:
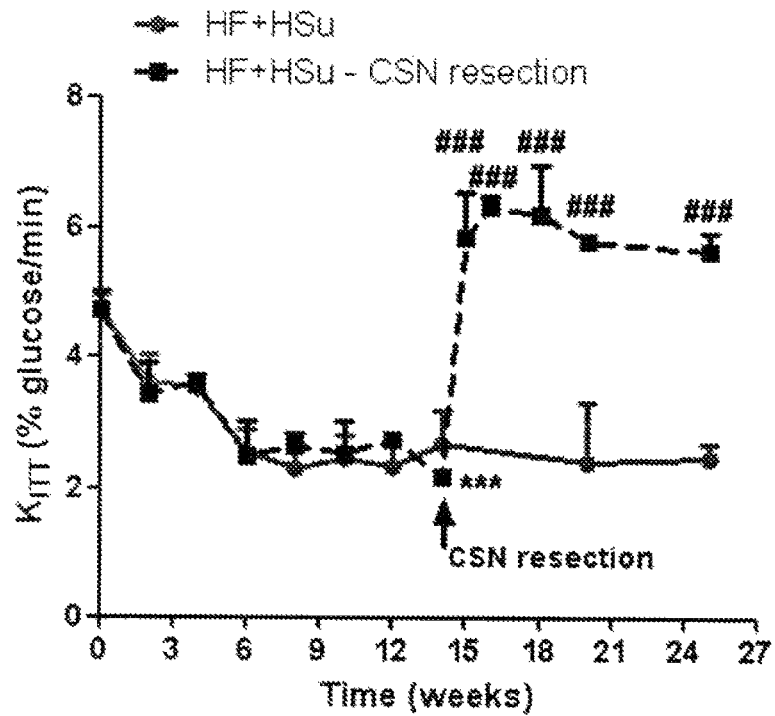
FIG. 3: Effect of chronic carotid sinus nerve (CSN) bilateral denervation on insulin sensitivity determined by the insulin tolerance test, expressed as the constant rate for glucose disappearance ($K_{ITT}$). CSN resection was performed after 14 weeks of HF+HSu diet (type II diabetic rat model). One-way ANOVA with Dunnett's multiple comparison test. ***p<0.001, vs values in animals at 0 weeks of diet. ###p<0.001, vs values in animals at 14 weeks of diet (before CSN resection). Data represent means±SEN.

FIG. 2 shows the effect of the HF+Hsu diet on insulin sensitivity. Type 2 diabetic rats exposed to the HF+Hsu diet exhibit a significantly diminished rate for the clearance of glucose compared to control rats fed a normal diet, thereby indicating a reduction in sensitivity to insulin (i.e. insulin resistance or tolerance) as a result of the HF+Hsu diet. Similarly, FIG. 4 shows that prediabetic mice exposed to the HF diet also exhibit a reduction in sensitivity to insulin. The ability of CSN resection to restore sensitivity to insulin in both type 2 diabetic and prediabetic models is shown in FIG. 3 and FIG. 4, respectively, where insulin resistant rats from both models that have undergone bilateral CSN resection exhibit insulin sensitivity comparable to control rats fed a normal diet.

Figure 12:
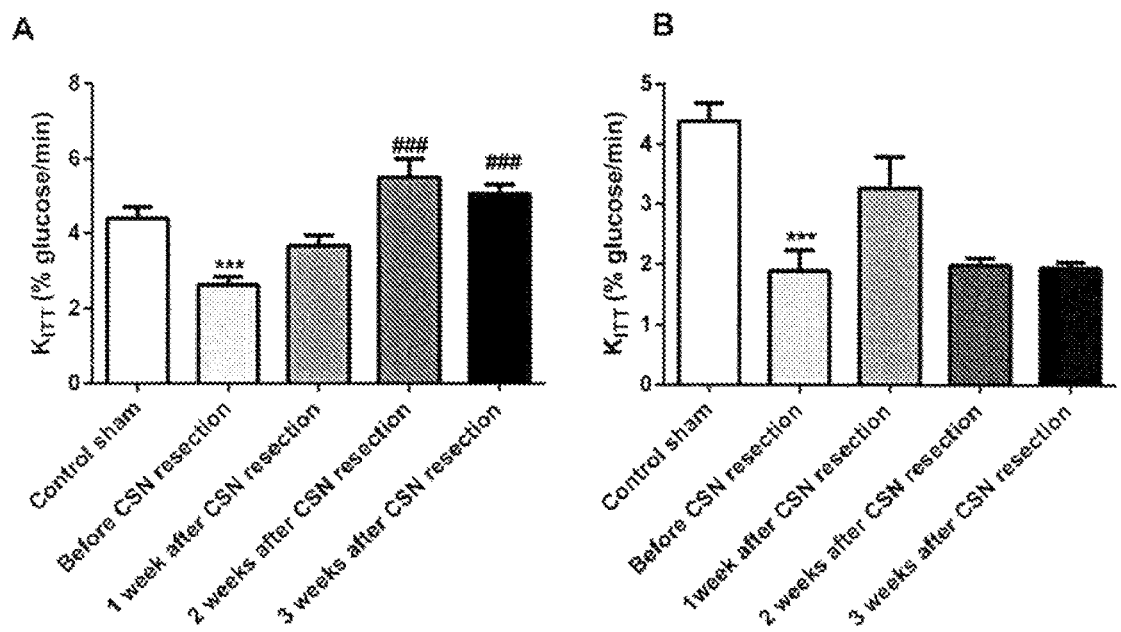
FIG. 12: Effect of bilateral (A) and unilateral (B) carotid sinus nerve (CSN) resection on insulin sensitivity in an animal model of prediabetes (Wistar rats submitted to 6 weeks of HF diet, with bilateral CSN denervation at 3 weeks). Insulin sensitivity was assessed, through an insulin tolerance test (ITT) and expressed by the constant of ITT ($K_{ITT}$), before, one, two and 3 weeks after CSN resection. CSN resection was performed after 3 weeks of HF diet.

FIG. 12 shows the effect of bilateral (A) and unilateral (B) CSN denervation on insulin sensitivity in prediabetic rats. FIG. 12B shows that insulin sensitivity is restored one week after unilateral denervation (i.e. only one CSN is resected). This effect is lost by 2 weeks post-denervation, likely due to compensation via increased activity in the other CSN. However, it is expected that a partial or temporary unilateral modulation of CSN neural activity (i.e. of only one CSN) would not result in such compensation. FIG. 12A shows that bilateral denervation effectively restores insulin sensitivity. This effect is maintained until at least 3 weeks post-denervation.

Measurement of Fasting Glucose and Glucose Tolerance

Glucose tolerance was evaluated by the oral glucose tolerance test (OGTT). A glucose solution (2 g/kg body weight) was administered intragastrically by oral gavage after an overnight fast (Carrascosa at al., 2001). Blood samples were collected by tail tipping and glucose levels were measured with a glucometer (Precision Xtra Meter, Abbott Diabetes Care, Portugal) and test strips (Abbott Diabetes Care, Portugal) at 0 (before the glucose load), 15, 30, 60, 120 and 180 min after glucose administration. The evaluation of the glycaemia response is performed by calculating the total area under the serum glucose curve using the minimum squares method or the trapezoidal method (Matthews et al., 1990). At the end of the OGTT blood was collected by the tail vein to eppendorfs. Serum samples were centrifuged in a microfuge (Eppendorf, Madrid, Spain) at 12,000×g for 10 min.

FIGS. 8 and 9 clearly show that a HF+Hsu diet greatly increases fasting glucose glycaemia in type 2 diabetic rats, both after 14 weeks and 25 weeks of the diet (FIG. 8), but that this hyperglycaemia is reduced when CSN neural activity is prevented (FIG. 9). FIG. 4 shows that a HF diet does not affect glycaemia in prediabetic rats, in accordance with the model of prediabetes.

Overall tolerance of glucose is also impaired in type 2 diabetic rats fed a HF+Hsu diet. FIG. 10A shows that the total area under the glucose response curve for these type 2 diabetic rats is much higher than for controls, both at 14 and 25 weeks, indicating an impaired response to glucose. In FIG. 10B it is shown that for rats which have undergone CSN denervation after 14 weeks of a HF+Hsu diet, the area under the response curve is smaller. This demonstrates that it is possible to improve the glucose response by preventing CSN neural activity in type 2 diabetics.

Terminal Experiment

At the end of the experiments, mean arterial pressure was monitored in the femoral artery (Conde et al., 2012; Guarino et al., 2013, which are incorporated herein by reference). After, the rats were killed by an intracardiac overdose of pentobarbital, except when heart puncture was performed to collect blood. This terminal experiment was performed with animals under sodium pentobarbital (60 mg/kg i.p.) anesthesia, since pentobarbital was shown not to alter the metabolic parameters tested herein (constant rate for glucose disappearance ($K_{ITT}$), fasting glycemia, insulinemia, and free fatty acids) in comparison with conscious animals (Guarino et al., 2013) or insulin responses to glucose (Davidson, 1971, incorporated herein by reference).

Measurement of Body Weight and Fat Mass

Figure 6:
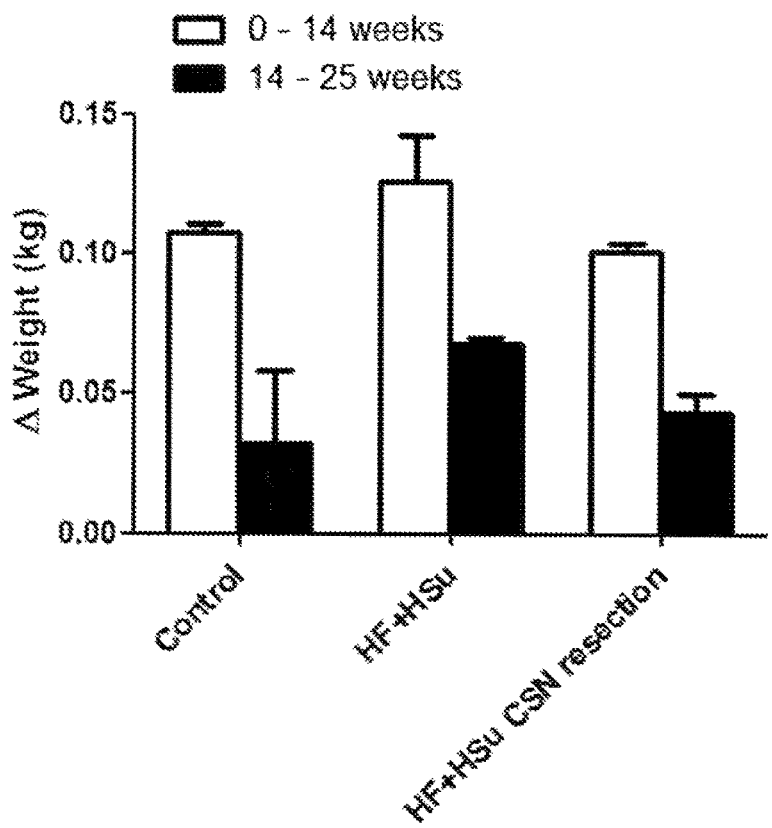
FIG. 6: Effect of chronic carotid sinus nerve (CSN) bilateral denervation on body-weight increment between 0-14 weeks and between 14-25 weeks in control animals and in animals submitted to hypercaloric diets (High-fat (HF)+ high sucrose (HSu)). CSN resection was performed after 14 weeks of HF+HSu diet. Data represent means±SEM.

Body weight of type 2 diabetic rats was assessed twice per week (FIG. 6). These animals (fed a HF+Hsu diet) exhibited reduced weight gain following CSN denervation compared to those animals on a HF+Hsu diet without CSN denervation (FIG. 6).

Figure 7:
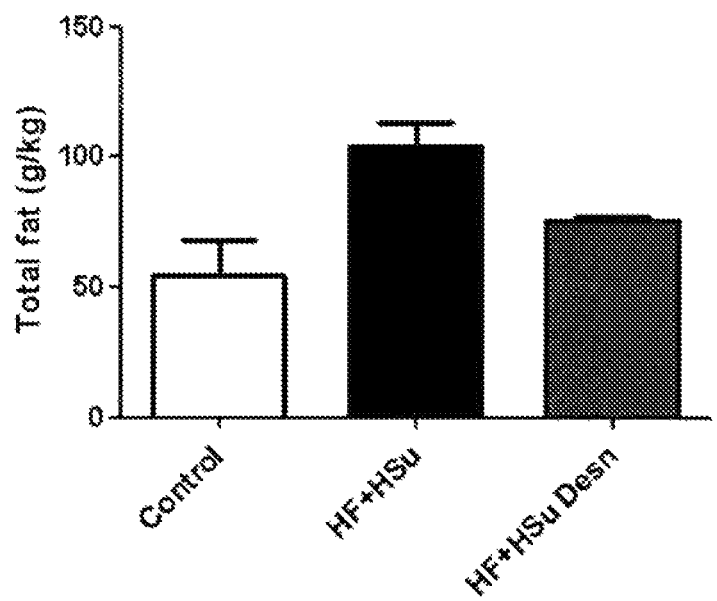
FIG. 7: Effect of bilateral carotid sinus nerve denervation on (A) total, (B) subcutaneous and (C) visceral fat in animal model of type II diabetes (Wistar rats submitted to 14 and 25 weeks of HF+Hsu diet, with bilateral CSN denervation at 14 weeks). Data represent means±SEM.
Figure 7:
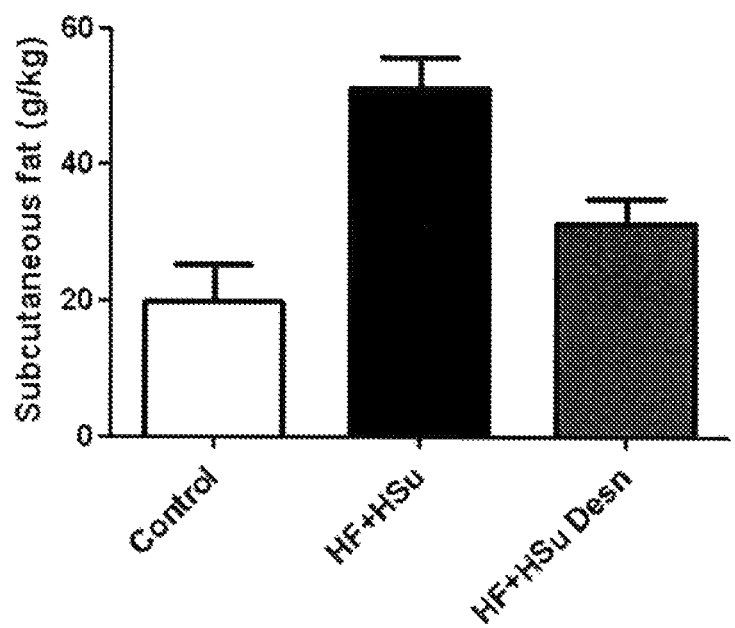
Figure 7C:
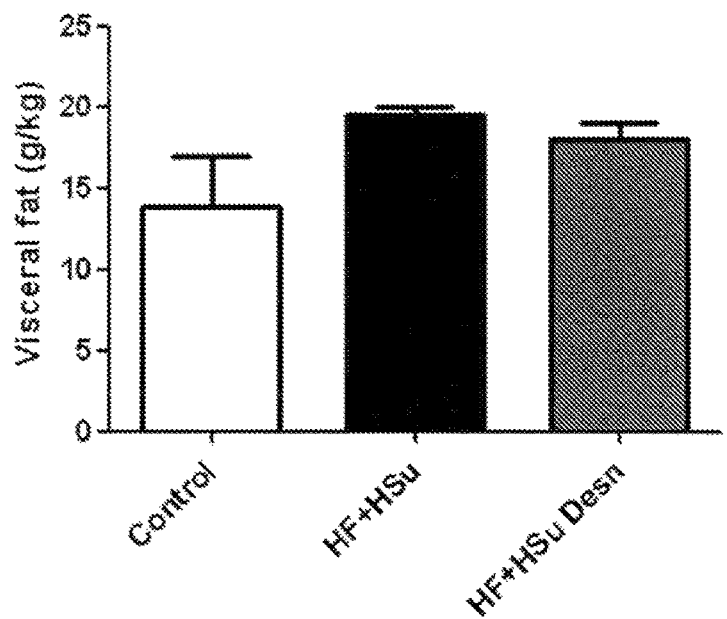

Total, subcutaneous and visceral fat were collected after an abdominal laparotomy and weighed (FIG. 7). Type 2 diabetic rats (fed a HF+Hsu diet for 25 weeks) exhibited an increase in total fat compared to control animals. Type 2 diabetic rats that had undergone CSN denervation at 14 weeks exhibited reduced fat gain compared to those that had not undergone denervation (FIG. 7). In particular, rats in which CSN neural activity was prevented exhibited a significant reduction in the level of subcutaneous fat accumulated (FIG. 7B).

As shown in Table 1, prediabetic rats (fed a HF diet for 6 week) that had undergone CSN resection after 3 weeks of HF diet exhibited significantly reduced weight gain, had reduced total fat mass and had reduced visceral fat mass compared to prediabetic animals that had not undergone CSN denervation (Table 1). Denervated HF-diet rats also had lower levels of low density lipoprotein (LDL) and triglycerides compared to HF-diet rats which had not been denervated, as well as higher levels of high density lipoprotein (HDL).

TABLE 1

| | Treatments | | | |
|---|---|---|---|---|
| | Control | | High-Fat Diet | |
| | Without CSN resection | With CSN resection | Without CSN resection | With CSN resection |
| Weight gain (g/day) | 0.68 ± 0.2 | 0.38 ± 0.2 | 1.43 ± 0.3* | 0.07 ± 0.3### |
| Total fat (g/kg) | 51.7 ± 2.4 | 47.4 ± 6.3 | 70.1 ± 3.6** | 64.7 ± 6.3 |
| Visceral fat (g/kg) | 9.9 ± 0.4 | 9.5 ± 0.6 | 13.8 ± 0.8*** | 11.8 ± 0.9# |
| Total cholesterol (mg/dl) | 71.9 ± 3.9 | 68.6 ± 5.0 | 67.6 ± 2.9 | 69.6 ± 2.9 |
| LDL (mg/dl) | 4.9 ± 0.3 | 5.3 ± 0.6 | 4.2 ± 0.5 | 3.8 ± 0.8 |
| HDL (mg/dl) | 28.0 ± 1.2 | 23.9 ± 1.2 | 20.3 ± 1.2*** | 25.0 ± 1.9# |
| Triglycerides (mg/dl) | 31.1 ± 3.5 | 20.4 ± 2.7 | 45.4 ± 3.4* | 19.8 ± 5.3## |

Effect of carotid sinus nerve resection on weight, total fat, visceral fat and lipid profile (total cholesterol, triglycerides, HDL and LDL) in control and high fat diet rats. Data with and without carotid sinus resection are means of 8-9 and 8-10 values, respectively. One and Two-way ANOVA with Dunnett's and Bonferroni multicomparison tests, respectively;
*p < 0.05 and
***p < 0.001 vs control;
p < 0.01 and
p < 0.001 comparing values with and without CSN resection.

This shows that by preventing CSN neural activity, it is possible to reduce the rate of weight gain, accumulation of fat mass and also improve the blood lipid profile in models of prediabetes. Notably, the circulating triglyceride content was reduced in resected rats versus those which had CSN intact in both the control and high-fat diet groups. This suggests that the device and methods of the Invention could be utilized to reduce circulating triglyceride content.

Measurement of Plasma Insulin, HbA1c, Circulating Free Fatty Acids and Catecholamines Levels, Adrenal Medulla and Renal Catecholamine Content.

Insulin concentrations are quantified with an enzyme-linked immunosorbent assay (ELISA) kit (Mercodia Ultrasensitive Rat Insulin ELISA Kit, Mercodia ASB, Uppsala, Sweden), HbA1c is assessed using a RANDOX kit (RANDOX, Irlandox, Porto, Portugal), free fatty acids with a colorimetric assay (Zenbio, North Carolina, USA) and corticosterone determination performed with a DetectX corticosterone Immunoassay kit (Arbor Assays, Madrid, Spain).

For catecholamine quantification in plasma, 400 mL plasma samples are purified and catecholamines extracted and quantified as described in Conde et al., 2012a, which is incorporated herein by reference. For quantification of catecholamine content in adrenal medulla, adrenal medullas previously frozen are homogenized in 0.6 N PCA, and their endogenous catecholamine content was quantified as described in Gallego-Martin et al., 2012, which is incorporated herein by reference.

Recordings of Carotid Sinus Nerve Activity Ex Vivo

Rats from control and prediabetes groups were anaesthetized with sodium pentobarbital (Sigma, Madrid, Spain) (60 mg/kg i.p.), tracheostomized and the carotid arteries were dissected past the carotid bifurcation. The preparation CB-CSN was identified under a dissecting microscope and a block of tissue, including the carotid bifurcation and the glossopharyngeal nerve, was removed and placed in a Lucite chamber in ice-cold/100% O2-equilibrated Tyrode (in mM: NaCl 140; KCl 5; CaCl2 2; MgCl2 1.1; HEPES 10; glucose 5.5; pH 7.40) for the further dissection. Once surgically cleaned of unwanted surrounding tissue, the preparation CB-CSN was digested during 3-5 min in collagenase type I (1 mg/ml) solution to loosen the perineurium (Conde at al. 2012b, incorporated herein by reference). The CB-CSN preparation was maintained in ice-cold 100% O2-equilibrated Tyrode until it was transferred to the recording chamber. In all instances animals were killed by intracardiac overdoses of sodium pentobarbital until the beating of their hearts ceased.

The CS-CSN preparation was transferred to a recording chamber mounted on a dissection microscope (Nikon Corporation, Tokyo, Japan) and superfused (37° C.) with bicarbonate/CO2-buffered saline (in mM: NaCl 120; NaHCO3 24; KCl 3; CaCl2 2; MgCl2 1.1; glucose 10; pH 7.40). Recordings of either a single or a few fibers of CSN were made using a suction electrode. The pipette potential was obtained with a 5K gain, filtered at low frequency (5 Hz) and high frequency (5 kHz), and recorded at a sample frequency of 200 μsec (Digidata 1550, pClamp; Axon Instruments, Molecular Devices, Wokingham, UK) and stored on a computer. Chemoreceptor activity was identified (as the spontaneous generation of action potentials at irregular intervals) and confirmed by its increase in response to hypoxia (normoxia: 20% O2+5% O2+75% N2; hypoxia: 5% O2+5% CO2+balanced N2 or 0% O2 5% CO2+balanced N2). CSN unit activity was converted to logic pulses, which were summed every second and converted in a voltage proportional to the sum (FIG. 11).

FIG. 11 clearly shows that prediabetic rats (i.e. those that have been fed the HF diet for 3 weeks) exhibit a different pattern of action potentials in the CSN in response to stimuli. This indicates that the pathological symptoms of insulin resistance, weight gain and impaired response to glucose are associated with a change in neural activity in the CSN. Moreover, it is clear from the data described above that preventing this abnormal neural activity in the CSN results in an improvement in the diabetes-associated symptoms in these rats. It is therefore possible to treat conditions associated with an impaired response to glucose and with insulin sensitivity (e.g. type 2 diabetes) by modulating the neural activity in the CSN, for example by blocking or inhibiting the signalling, or by altering the signalling pattern to more closely resemble that of a healthy subject. Such modulation can be performed by a neuromodulation device.

Terminal Studies of Bilateral CSN Blocking

Figure 13:
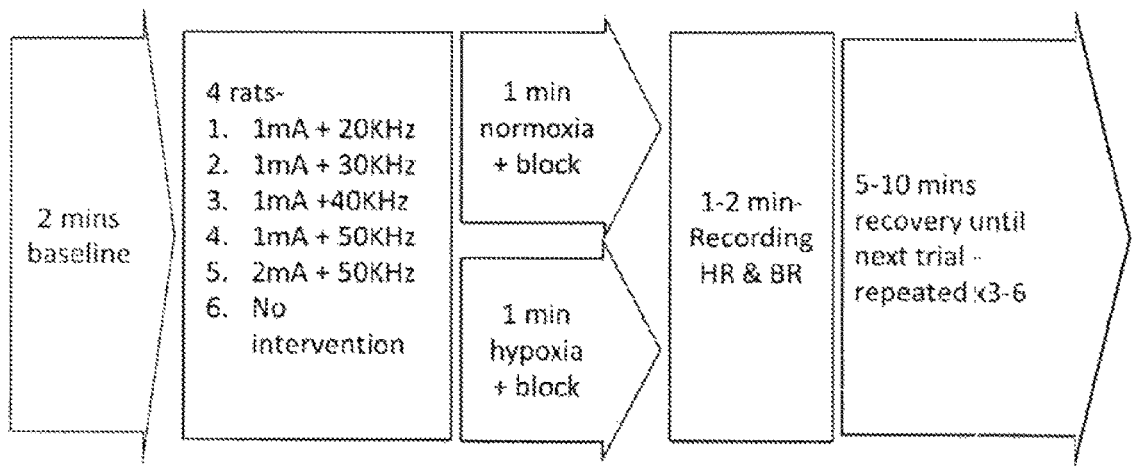
FIG. 13: Process flow for terminal studies of bilateral CSN blocking, and process for determining efficacious blocking parameters.

FIG. 13 shows a flow chart indicating the process followed for the experiments described below.

Rats fed a normal diet were anaesthetised with urethane (I.P. 1.5 g/kg). EMG electrodes were implanted subcutaneously across the diaphragm. The CSN was bilaterally exposed and dissected from underlying tissue. CorTec cuff electrodes (1 mm×1 mm, bipolar platinum iridium electrodes, AirRay microcuff sling technology) were implanted bilaterally on each CSN. Tisseel Fibrin glue was used to both secure and insulate the area. This glue prevents excess current spread and off target muscular twitches and jaw clenching.

In order to confirm effective block of CSN neural signalling, hypoxia was used as a surrogate model, as detection of hypoxia by the carotid body leads to neural activity in the CSN. Changes in heart rate and breathing rate were measured as indicative of a response to detected hypoxia. Effective block of neural activity was indicated by a reduction in the relative changes of heart and breathing rate in response to hypoxia.

A dose response to high frequency alternating current (HFAC) was used to determine the effective parameter of block. The tested blocking signals were 20 KHz, 30 KHz, 40 KHz and 50 KHz, each at 1 mA.

Figure 14:
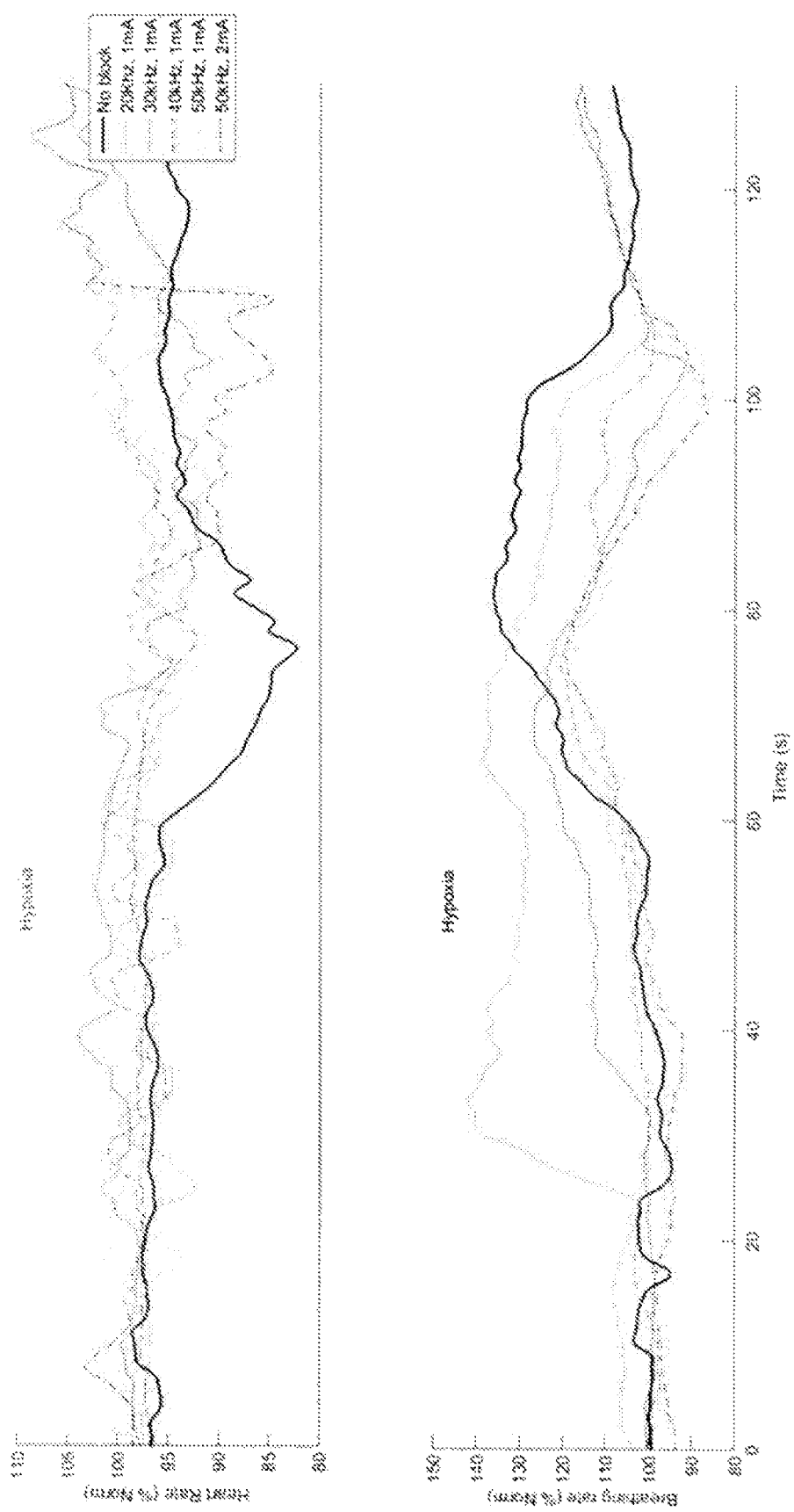
FIG. 14: Responses through time of cardiorespiratory function to hypoxia with and without HFAC nerve conduction block

Rats were then subjected to 10% $O_2$ in $N_2$ to induce hypoxia and baseline responses to hypoxia were recorded. Data was recorded by EMG and ECG from the surface electrodes and analysed in MatLab to quantify the heart rate and breathing rate response. Hypoxia led to a delayed (by approximately 30 seconds) increase in respiratory rate and a reduced heart rate (FIG. 14—no block). After baseline responses to hypoxia were collected, a dose response to HFAC was used to determine the effective parameter of block. The blocking signals were 20 KHz, 30 KHz, 40 KHz, each at 1 mA, and 50 KHz at 1 and 2 mA current (FIG. 14).

Figure 15:
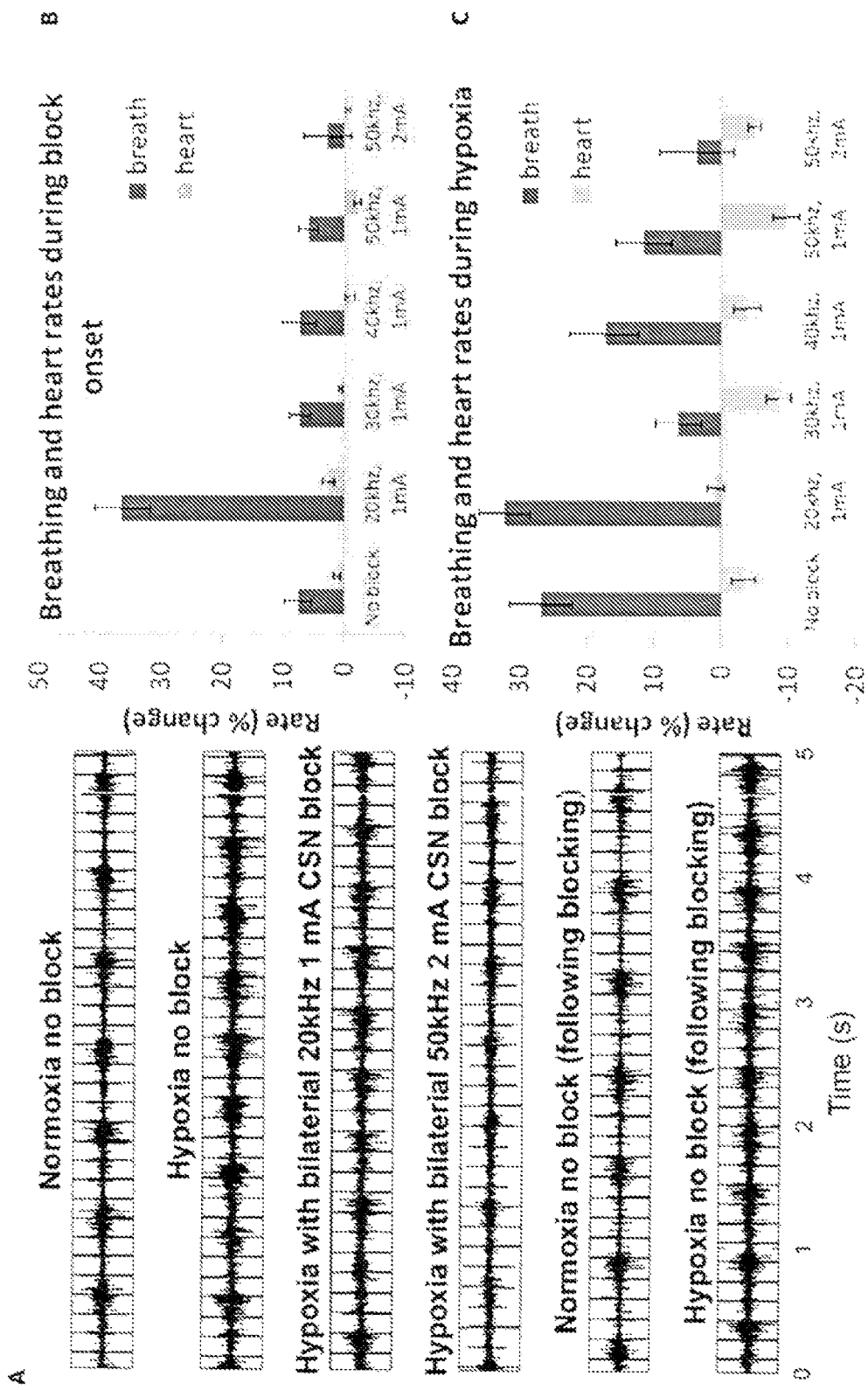
FIG. 15: A. Example raw data traces of EMG and ECG. B Onset responses due to HFAC. C. Quantitative respiratory rate change to hypoxia with and without HFAC.

When quantified (FIG. 15B), none of the stimulation parameters tested produced 100% inhibition of the hypoxia response, likely due to the compensatory effect of the central and aortic arch chemoreceptors. An onset response indicated by an increase in breathing rate was observed with a signal of 20 KHz 1 mA (FIG. 15B). No or minimal onset response was observed for the other blocking signals (FIG. 15B). During exposure to hypoxia, 30 KHz 1 mA, 40 KHz 1 mA and 50 KHz 1 mA and 50 KHz 2 mA all resulted in an effective block of CSN activity, indicated by reduce relative changes in breathing and heart rate in response to hypoxic conditions (FIG. 15C).

Reversibility of the block induced by each blocking signal was observed by reassessing responses to hypoxia 1 minute post-block compared to baseline responses (FIG. 15A).

Figure 16:
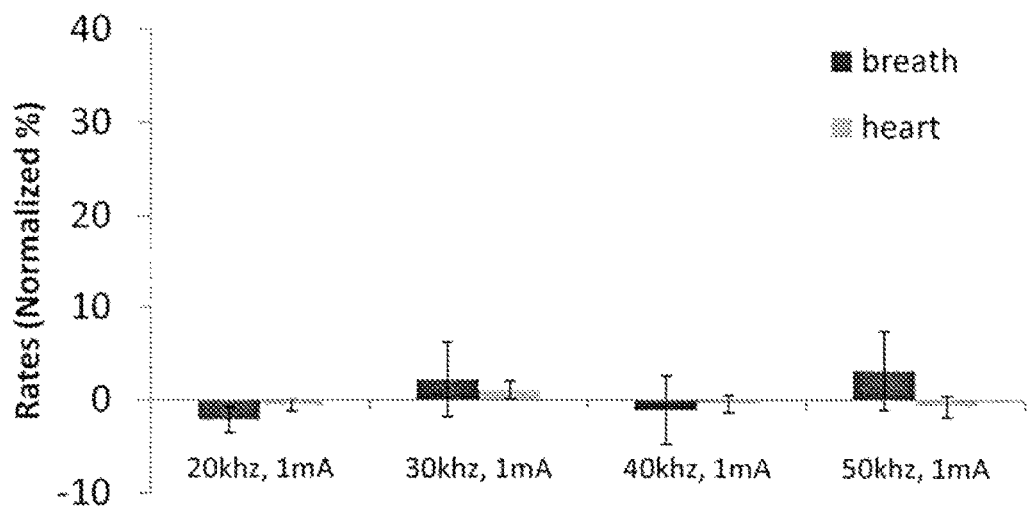
FIG. 16: Quantification of heart and breathing rate changes induced by HFAC blocks under normoxia.

No effect of HFAC between 20-50 KHz was found on baseline respiratory and cardiac responses in the normoxic setting (FIG. 16).

Surgical Implantation and Recovery Studies

Rats fed a normal diet were anaesthetised with ketamine/medetomidine (I.P.). Head caps were implanted on the skull, attached to the CorTec cuff electrodes, and trocarred behind the ear and connected bilaterally to the CSNs, and insulated in place by Fibrin glue. Immediately after implantation animals were stimulated briefly (2 seconds) with 300 uA at 5 Hz to determine correct electrode placement—indicated by increase in breathing rate (this was observed in all animals). Animals were allowed to recover for 10 days prior to tethered blocking.

At 10 days animals were tethered (and acclimatised for 2 days) and then exposed to a blocking signal of 50 KHz 2 mA sinusoid HFAC continuously for 7 days. No behavioural alterations were shown.

Figure 17:
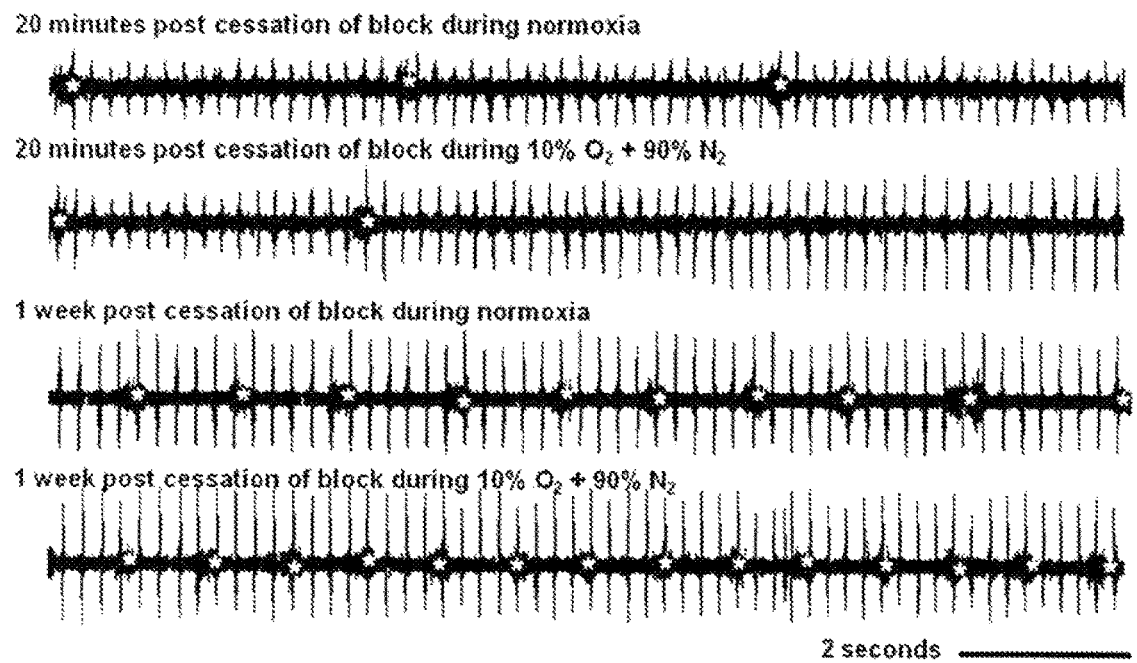
FIG. 17: Data traces of EMG and ECG 20 minutes and 1 week post cessation of continuous bilateral carotid sinus nerve block 50 Hz, 2 mA stimulus.

Following cessation of electrical signal, animals were exposed to a hypoxic stimulus and respiratory rate was evaluated twice; at 20 mins post-signal and after one week. At 20 minutes following cessation of electrical signal, the animals did not respond to a hypoxia (10% O2+90% nitrogen) challenge, demonstrating that a functional block was maintained (FIG. 17). One week after the electrical stimulus was stopped, the response to hypoxia had returned to baseline levels (increase in respiratory rate of –20%), indicating the reversibility of the functional electrical block (FIG. 17). The reversibility of the functional block confirms that the functional block produced by electrical signal was not due to damage to the CSN.

Efficacy Studies

Figure 18:
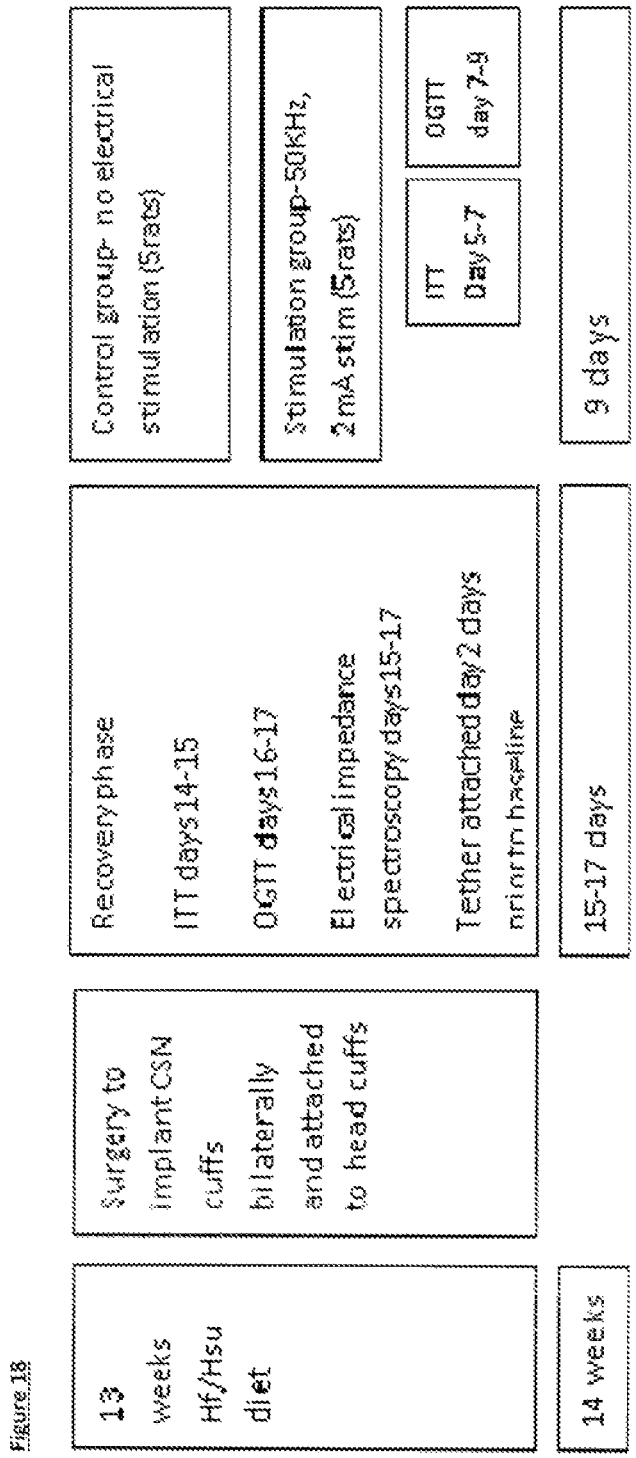
FIG. 18: Description of study flow for surgical implantation and recovery in disease model, to evaluate insulin and glucose tolerance

Rats underwent ITT and GTT challenges at the baseline, (prior to Hf+Hsu diet) prior to surgery, post-surgery, prior to randomisation and after sham or active intervention (see FIG. 18 for flow series of events). Animals were anaesthetised with ketamine/medetomidine (I.P.) and head caps were implanted and attached to the CorTec cuff electrodes and trocarred behind the ear and connected bilaterally to the CSNs, and insulated in place by Fibrin glue. Electrical impedance spectroscopy was conducted on days 14 and 15 post surgery. ITT was performed between days 14-15, and OGTT between days 16-17 post surgery.

Figure 19:
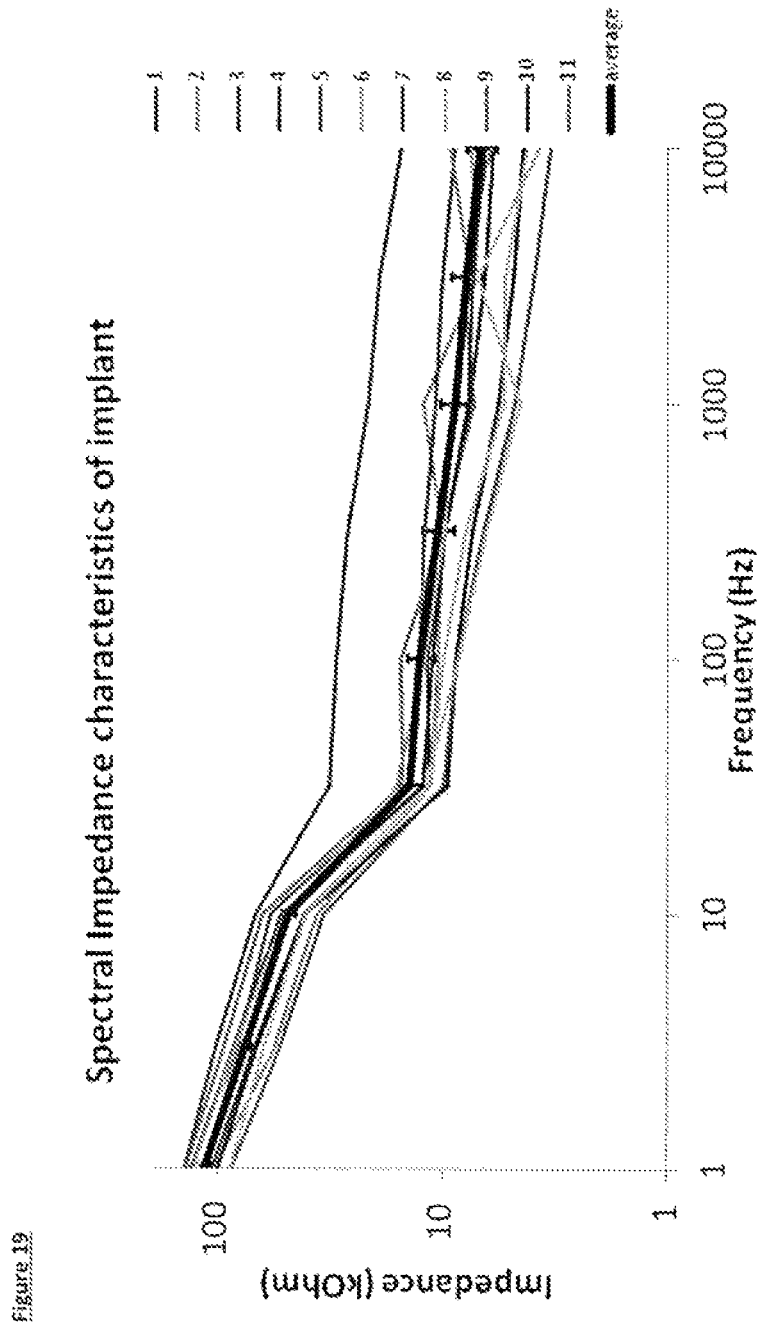
FIG. 19: Electrode functional impedance measurements at 10 days implantation show that the implants are appropriate and stable; both acutely and at 10 days post implantation. Results are shown on a logarithmic y-axis

The electrical impedance spectroscopy results at 10 days post cuff electrode implantation confirmed that the electrodes were positioned correctly upon the nerves, and functioning as expected for their geometry and material composition (average–8.8 Kohms [+/–1.5 Kohms] at 1 KHz) (FIG. 19).

Post-surgical KITT, calculated from the ITT taken on post-operative days 14-15 confirmed that that surgery had minimal impact upon KITT levels (FIG. 20). AUC of OGTT performed on days 16-17 confirmed that glycaemic response to a stimulus was not impacted by surgery.

TABLE 2

Oral glucose challenge test: Area under the curve (AUC) of glycaemia (mg/dl)

| | Before diet | 13 weeks of diet | Post surgery (pre- block) |
|---|---|---|---|
| AUC sham intervention group | 21437 | 24914 | 23960 |
| AUC electrical block, active intervention group | 22395 | 24464 | 24354 |

Animals were attached to tethers to allow acclimatisation for 2 days prior to randomisation. Animals were then randomised into two groups: active intervention group (electrical blocking of the CSN using 50 KHz (2 mA)) or sham intervention group (no electrical block of the CSN). ITT was performed on days 5-7 and OGTT performed on days 7-9.

7-9 days post randomisation, ITT was performed on all animals from both groups and KITT calculated (FIG. 20). The mean KITT of animals in the sham intervention group increased by 18.46% during the intervention period. This increase was not statistically significant (p=0.4448). The KITT of animals in the active intervention group increased by 47.36% during the intervention period. Thin increase was statistically significant (p=0.0128). A trend of increasing KITT with longer duration of block was observed (FIG. 20)

5 days post randomisation. OGTT was performed on 2 animals from the active intervention group. 7 days post randomisation, OGTT was performed on all animals from the sham intervention group and the remaining 3 animals from the active intervention group. The mean glycaemia, area under the curve (AUC) of animals in sham intervention group increased by 1.12% during the intervention period. This increase was not statistically significant (p=0.6197). The AUC of animals in the active intervention group decreased by 21.41% during the intervention period. This decrease was statistically significant (p=0.0063).

This demonstrates a statistically significant improvement in glucose tolerance in the active intervention group, with glucose tolerance achieving greater than pre-diet levels (FIG. 21).

Thus, block of neural signalling in the carotid sinus nerve, in particular block using an electrical signal, results in statistically significant improvements in glucose tolerance and statistically significant improvements in insulin sensitivity.

TABLE 3

KITT (% glucose/min) for active and sham-intervention groups

| | KITT | |
|---|---|---|
| | Sham-intervention, no electrical block group N = 5 | Electrical block, active intervention group N = 5 |
| Before blocking | 2.592 | 2.874 |
| 7 days | 2.996 | 4.106 |
| Change (95% CI) | 0.40 (−0.92:1.73) | 1.232 (0.434:2.030) |
| Adjusted % change (95% CI) | 18.46 (−28.51:65.44) | 47.38 (5.829:88.94) |
| P value | 0.4448 | 0.0128 |

TABLE 4

Oral glucose tolerance test (OGTT) area under the curve (AUC) for glycaemia following randomization

| | Sham-intervention, no electrical block group N = 5 | Electrical block, active intervention group N = 5 |
|---|---|---|
| Post surgical, pre-intervention AUC (mg/dl) | 23960 | 24354 |
| Post intervention glycaemia AUC (mg/dl) 5-7 days | 23690 | 19139 |
| Change from baseline (95% (CI)) | −270 (−1666:1126) | −5215 (−8132:−2503) |
| % change from baseline (95% CI) | −1.12% (−7.063:4.951) | −21.41% (−32.66:−10.53) |
| P value | 0.6197 | 0.0063 |

The invention claimed is:

1. A device for inhibiting the neural activity of a carotid sinus nerve (CSN) or carotid body of a subject, the device comprising:
   one or more electrodes configured to apply an electrical signal to the CSN or associated carotid body of the subject; and
   a controller coupled to the one or more electrodes, the controller controlling the electrical signal to be applied by the one or more electrodes, such that the electrical signal inhibits the neural activity of the CSN or carotid body to produce a physiological response in the subject,
   wherein the physiological response is one or more of the group consisting of: an increase in insulin sensitivity in the subject, an increase in glucose tolerance in the subject, a decrease in plasma glucose concentration in the subject, a reduction in subcutaneous fat content in the subject, and a reduction in obesity in the subject,
   wherein the electrical signal comprises an alternating current (AC) waveform of 0.5 to 100 kHz frequency.

2. A device according to claim 1, wherein the AC waveform has a frequency of 30-50 kHz.

3. A device according to claim 2 where the electrode is a cuff electrode.

4. A device according to claim 2 where the electrode is a bipolar cuff electrode.

5. A device according to claim 2, wherein the device is suitable for at least partial implantation into the subject.

6. A device according to claim 2, wherein the device is suitable to be wholly implanted into the subject.

7. A device according to claim 1 where the electrode is a cuff electrode.

8. A device according to claim 1 where the electrode is a bipolar cuff electrode.

9. A device according to claim 1, wherein the device is suitable for at least partial implantation into the subject.

10. A device according to claim 1, wherein the device is suitable to be wholly implanted into the subject.

11. A device according to claim 1 wherein the signal comprises an alternating current (AC) waveform of greater than 25 kHz frequency.

12. A device according to claim 11 where the electrode is a cuff electrode.

13. A device according to claim 11 where the electrode is a bipolar cuff electrode.

14. A device according to claim 11, wherein the device is suitable for at least partial implantation into the subject.

15. A device according to claim 11, wherein the device is suitable to be wholly implanted into the subject.

16. A device according to claim 1 wherein the signal comprises an alternating current (AC) waveform of at least 30 kHz frequency.

17. A device according to claim 16 where the electrode is a cuff electrode.

18. A device according to claim 16 where the electrode is a bipolar cuff electrode.

19. A device according to claim 16, wherein the device is suitable for at least partial implantation into the subject.

20. A device according to claim 16, wherein the device is suitable to be wholly implanted into the subject.

21. A method of inhibiting neural signalling in the CSN of a subject comprising:
   i. implanting in the subject a device for inhibiting the neural activity of a carotid sinus nerve (CSN) or carotid body of a subject, the device comprising:
      one or more transducers configured to apply a signal to the CSN or associated carotid body of the subject; and
      a controller coupled to the one or more transducers, the controller controlling the signal to be applied by the one or more transducers, such that the signal inhibits the neural activity of the CSN or carotid body to produce a physiological response in the subject,
      wherein the physiological response is one or more of the group consisting of: an increase in insulin sensitivity in the subject, an increase in glucose tolerance in the subject, a decrease in plasma glucose concentration in the subject, a reduction in subcutaneous fat content in the subject, and a reduction in obesity in the subject;
   ii. positioning at least one transducer of the device in signalling contact with a CSN or carotid body of the subject;
   iii. activating the device,
      wherein a first transducer is positioned in signalling contact with the left carotid sinus nerve (CSN) and/or left carotid body of said subject to modulate the neural activity of the left CSN in the subject, and a second transducer is positioned in signalling contact with the right carotid sinus nerve (CSN) and/or right carotid body of said subject to modulate the neural activity of the right CSN in the subject.

22. A method of treating a condition associated with impaired glucose control in a subject, the method comprising applying a signal to a part or all of a carotid sinus nerve (CSN) and/or a carotid body of said subject to inhibit the neural activity of a CSN in the subject,
   wherein the signal is an electrical current and, when the signal is applied by a neuromodulation device comprising one or more transducers for applying the signal, each transducer configured to apply the signal is an electrode,
wherein the signal comprises an alternating current (AC) waveform of 0.5 to 100 kHz frequency.

23. A method according to claim 22, wherein the AC waveform has a frequency of 30-50kHz.

* * * * *